United States Patent [19]

Tahara et al.

[11] Patent Number: 5,567,621
[45] Date of Patent: Oct. 22, 1996

[54] METHOD OF AND APPARATUS FOR ANALYZING NITROGEN COMPOUND AND PHOSPHORUS COMPOUND CONTAINED IN WATER

[75] Inventors: Shu Tahara, Shiga; Yauzo Morita, Kyoto, both of Japan

[73] Assignee: Shimadzu Corporation, Kyoto, Japan

[21] Appl. No.: 272,747

[22] Filed: Jul. 11, 1994

[30] Foreign Application Priority Data

| Jul. 14, 1993 | [JP] | Japan | 5-197964 |
| Jul. 14, 1993 | [JP] | Japan | 5-197965 |
| Nov. 30, 1993 | [JP] | Japan | 5-330042 |
| Apr. 30, 1994 | [JP] | Japan | 6-114236 |
| May 16, 1994 | [JP] | Japan | 6-126769 |

[51] Int. Cl.$^6$ .................................................. G01N 21/78
[52] U.S. Cl. ................ 436/103; 436/106; 436/110; 436/114; 436/164; 436/171
[58] Field of Search .............................. 436/103, 106, 436/114, 110, 164, 171; 422/24, 190, 198, 186

[56] References Cited

U.S. PATENT DOCUMENTS

| H406 | 1/1988 | Wohltjen | 436/153 |
| 2,697,651 | 12/1954 | Gutzeit | 436/103 |
| 3,226,201 | 12/1965 | Harmon | 422/190 |
| 3,607,070 | 9/1971 | Stenger et al. | 436/103 |
| 3,924,139 | 12/1975 | Hirose et al. | 250/527 |
| 4,008,136 | 2/1977 | Williams | 204/158 R |
| 4,437,954 | 3/1984 | Sammells et al. | 204/129 |
| 4,591,505 | 5/1986 | Hateman et al. | 435/4 |
| 4,599,316 | 7/1986 | Hahn et al. | 436/105 |
| 4,883,579 | 11/1989 | Humphries et al. | 204/403 |
| 5,244,811 | 9/1993 | Matthews | 436/104 |
| 5,252,486 | 10/1993 | O'Lear et al. | 436/52 |
| 5,260,036 | 11/1993 | Weigold | 422/186.3 |
| 5,270,216 | 12/1993 | Kan et al. | 436/103 |
| 5,318,894 | 6/1994 | Pvgia | 435/28 |

FOREIGN PATENT DOCUMENTS

| 77-82148Y | 10/1977 | European Pat. Off. . |
| 55-159141 | 3/1981 | Japan . |
| 60-178353 | 1/1986 | Japan . |
| 61-071355 | 4/1986 | Japan . |
| 62-232542 | 10/1987 | Japan . |

Primary Examiner—Robert J. Warden
Assistant Examiner—N. Bhat
Attorney, Agent, or Firm—Nikaido, Marmelstein, Murray & Oram LLP

[57] ABSTRACT

Sample water is supplied to an oxidative decomposer, heated to 90° C. under presence of a photooxidation catalyst, and irradiated with ultraviolet radiation by a low pressure mercury lamp while being supplied with air, to cause photooxidative decomposition reaction. After the reaction, nitric acid ions are measured with an absorption photometer at a wavelength of 220 nm. Then, a color developer is added to the sample water, and the colored solution is employed for measurement of phosphoric ions with the absorption photometer at a wavelength of 880 nm.

15 Claims, 25 Drawing Sheets

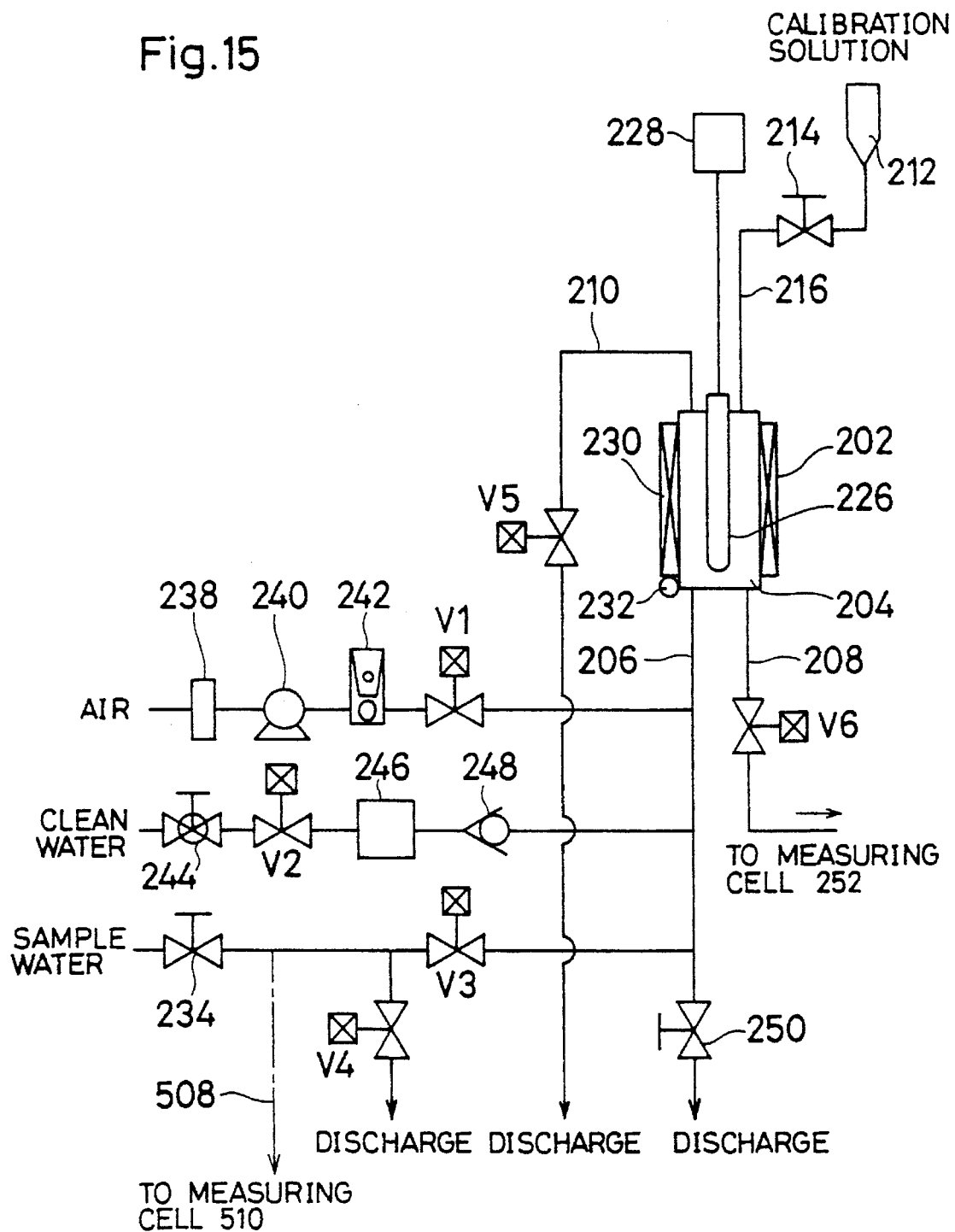

METHOD OF AND APPARATUS FOR ANALYZING NITROGEN COMPOUND AND PHOSPHORUS COMPOUND CONTAINED IN WATER

BACKGROUND OF THE INVENTION

1. Field of the Invention

The present invention relates to a method of analyzing small quantities of a nitrogen compound and a phosphorus compound which are contained in industrial waste water from a factory or the like, or environmental water such as river or lake, and an apparatus therefor.

2. Description of the Background Art

In Japan, a method of analyzing a nitrogen compound and a phosphorus compound which are contained in water is officially standardized under JIS K0102 and Notification No. 140 of the Environment Agency. A nitrogen compound which is contained in water exists in the form of nitric acid ions, nitrous acid ions, ammonium ions or organic nitrogen. While a TN (total nitrogen) analytical method of measuring total nitrogen which is contained in water is adapted to entirely convert the nitrogen compound to nitric acid ions to measure the same, it is difficult to oxidize ammonium ions and organic nitrogen into nitric acid ions. In TN measurement, therefore, an alkaline potassium peroxodisulfate solution is added to sample water, which in turn is heated at 120° C. for 30 minutes so that the nitrogen compound is entirely oxidized into nitric acid ions. Then the sample water is cooled and thereafter adjusted to pH 2 to 3, to be subjected to measurement of ultraviolet absorbance by nitric acid ions at a wavelength of 220 nm.

On the other hand, a phosphorus compound which is contained in water exists in the form of phosphoric acid ions, hydrolytic phosphorus, or organic phosphorus. In TP (total phosphorus) measurement, potassium peroxodisulfate is added as an oxidizer to sample water in a neutral state, and the sample water is heated at 120° C. for 30 minutes so that the phosphorus compound is entirely oxidized to phosphoric acid ions. Since phosphoric acid ions have no specific light absorption, an ammonium molybdate solution and an L-ascorbic acid solution are added as color developers to the sample water after cooling to color the same, thereby measuring absorbance at a wavelength of 880 nm.

Another TN measuring method is adapted to oxidize a nitrogen compound to nitric acid ions by an oxidation catalyst under a high temperature of at least 500° C. for measuring the same as nitrogen oxides by a chemiluminescence method, or to pass nitrogen oxides further through an oxidation-reduction reaction tube at about 600° C. and decompose the same to gaseous nitrogen for measuring the same as nitrogen by gas chromatography.

Still another method is adapted to supply ozone to sample water for oxidizing the same with ozone in an alkaline state in TN measurement or an acidic state in TP measurement.

There is no apparatus for analyzing TN measurement and TP measurement in sample water by a common analyzer. This is because pH conditions in oxidation with an oxidizer or ozone are different from each other such that a nitrogen compound is oxidized in an alkaline state while a phosphorus compound is oxidized in a neutral or acidic state.

In the oxidation method employing an oxidizer, sample water is heated to the high temperature of 120° C. exceeding its boiling point, and hence a pressure-resistant reaction kettle is required to complicate an oxidizing apparatus in structure and operation, leading to a high cost. Further, it is necessary to frequently supply the oxidizer as consumed, leading to a high running cost.

The method of oxidizing a nitrogen compound with a catalyst requires a high temperature of at least 500° C., and the catalyst is remarkably deteriorated. An apparatus therefor is complicated in structure such that the same is hard to maintain, while such an analytical method employing a catalyst is generally unsuitable for employment as a monitor on a job site.

The ozone oxidizing method requires a pH adjusting mechanism for oxidation of both nitrogen compound and phosphorus compound due to weak oxidation in a neutral area, and hence an apparatus therefor is complicated in structure. Further, acid and alkali pH adjusters are required as consumed products.

Thus, it is impossible to measure a nitrogen compound and a phosphorus compound in common by any conventional analytical method. Further, every one of the conventional methods requires a high cost and is hard to use due to insufficient fitness for a continuous monitor.

In Japan, the regulation of total emission has already been applied to organic pollutants which are contained in industrial waste water flowing into a closed sea area for the purpose of environmental protection of water quality, and COD(Chemical Oxygen Demand), TOC(Total Organic Carbon) and UV(Ultraviolet) meters are officially employed. Among these, the UV meter prevails most due to its simple structure. However, there is no apparatus for simultaneously measuring a nitrogen compound, a phosphorus compound and an organic pollutant.

SUMMARY OF THE INVENTION

An object of the present invention is to provide an analytical method which can measure a nitrogen compound and a phosphorus compound contained in sample water in common as well as continuously analyze the same for a long time.

Another object of the present invention is to provide an apparatus which is suitable for oxidizing both a nitrogen compound and phosphorus compound to convert the same to nitric acid ions and phosphoric acid ions in the aforementioned analytical method.

Still another object of the present invention is to provide an analyzer which can measure a nitrogen compound and a phosphorus compound contained in sample water in common as well as continuously analyze the same for a long time.

A further object of the present invention is to provide a measuring apparatus which can measure a nitrogen compound, a phosphorus compound and an organic pollutant contained in sample water in common by a single apparatus as well as continuously analyze the same for a long time.

An analytical method according to the present invention, which is adapted to analyze both a nitrogen compound and a phosphorus compound contained in water, comprises: (A) an oxidation step of heating sample water to a temperature of 50° to 100° C. while irradiating the same with ultraviolet radiation, (B) a step of measuring nitric acid ions contained in the oxidized sample water by absorptiometry, and (C) a step of adding a color developer selectively reacting with phosphoric acid ions to the oxidized sample water and measuring the colored solution by absorptiometry.

In the oxidation step (A), it is also possible to irradiate the sample water with ultraviolet radiation while blowing gas containing oxygen or ozone into the same. Alternatively, the sample water may be irradiated with ultraviolet radiation under presence of a photooxidation catalyst. While it is not requisite to blow gas containing oxygen or ozone in ultraviolet radiation irradiation in the case of using the catalyst, it is possible to increase the oxidizing velocity by blowing such gas. The photooxidation catalyst can be prepared from $TiO_2$ or silver halide such as AgCl, AgI or AgBr.

A photooxidative decomposer employed in the inventive analytical method comprises an oxidative reaction vessel having a sample water inlet, an ultraviolet radiation source for applying ultraviolet radiation into the oxidative reaction vessel, and heating means for heating the oxidative reaction vessel. The oxidative reaction vessel may be provided with a thin film of a photooxidation catalyst on its inner surface, or charged with photooxidation catalyst particles. When no photooxidation catalyst is employed, a gas supply port is preferably provided for blowing gas containing oxygen or ozone in irradiation with ultraviolet radiation. In such a photooxidative decomposer provided with a gas supply port, sample water stored in the oxidative reaction vessel is heated to 50° to 100° C. by the heating means and irradiated with ultraviolet which is emitted from the ultraviolet radiation source while the gas containing oxygen or ozone is blown into the sample water, so that both nitrogen compound and phosphorous compound contained in the sample water are oxidized to be converted to nitric acid ions and phosphoric acid ions respectively.

When a photooxidation catalyst is employed, on the other hand, the oxidizing velocity is increased and hence the photooxidative decomposer may be or may not be provided with the gas supply port for blowing the gas containing oxygen or ozone into the oxidative reaction vessel.

An analyzer according to the present invention comprises the aforementioned photooxidative decomposer, an absorbance measuring cell of quartz glass for measuring absorbance of sample water after oxidative reaction, a color developer adding passage for adding a color developer selectively reacting with phosphoric acid ions to the oxidative reaction vessel or the absorbance measuring cell, a light source part for applying a measuring beam to the absorbance measuring cell, separation means provided on a measuring beam transmitting path of the absorbance measuring cell for separating light transmitted therethrough into two optical paths, a first optical system provided on one of the optical paths for selecting an absorption wavelength specific to nitric acid ions and detecting light of this wavelength as sample light of nitric acid ions, a second optical system provided on another optical path for selecting an absorption wavelength specific to the color developer reacting with phosphoric acid ions and detecting light of this wavelength as sample light of phosphoric acid ions, and an arithmetic processing part for calculating nitrogen compound concentration and phosphorus compound concentration on the basis of detection signals from the first and second optical systems.

When the photooxidative decomposer employs a photooxidation catalyst, the oxidative reaction speed is so increased that it is possible to form a flow photooxidative decomposer continuously feeding sample water to the oxidative reaction vessel.

When gas containing oxygen or ozone is blown into the sample water, oxygen atoms or ozone may conceivably be generated in the water due to the following reactions which are caused when oxygen or ozone contained in the gas is irradiated with ultraviolet radiation:

$$O_2 + UV(185\ nm) \rightarrow 2O_2$$

$$O + O_2 \rightarrow O_3$$

$$O_3 + UV(254\ nm) \rightarrow O + O_2$$

The oxidative oxygen atoms or ozone oxidizes a nitrogen compound and a phosphorus compound contained in the sample water to convert the same to nitric acid ions and phosphoric acid ions respectively in the following manner:

$$(O, O_3) + (nitrogen\ compound, phosphorous\ compound) \rightarrow nitric\ acid\ ions, phosphoric\ acid\ ions$$

When an organic compound exists, oxygen atoms or ozone cuts unsaturated bonds of the organic compound.

$$((O, O_3) + unsaturated\ compound \rightarrow saturated\ compound, CO_2, H_2O$$

While ultraviolet absorption by unsaturated bonds interferes with specific absorption of nitric acid ions, such interference is removed when the unsaturated bonds are cut by oxygen atoms or ozone. For example, FIG. 1 shows an absorption spectrum (a) of sample water (1 ppm in nitrogen concentration) containing $NO_2C_6H_4OH$ before irradiation with ultraviolet radiation and another absorption spectrum (b) measured after irradiation with ultraviolet radiation with blow of air. The sample water not yet irradiated with ultraviolet radiation has the maximum absorption in the vicinity of about 340 nm, and exhibits ultraviolet absorption of the unsaturated bonds having an absorption band of not more than 400 nm. When the sample water is irradiated with ultraviolet radiation with blow of air to be subjected to photooxidative decomposition, the unsaturated bonds annihilate so that only a spectrum which is specific to nitric acid ions is detected. Thus, accuracy in nitric acid ion measurement is remarkably improved.

When a photooxidation catalyst is employed for the oxidative reaction vessel, it is conceivable that oxidative reaction is simultaneously caused by the photooxidation catalyst.

The sample water is heated to 50° to 100° C., since the photooxidative decomposition is remarkably facilitated by heating.

According to the present invention, a nitrogen compound and a phosphorus compound which are contained in the sample water are simultaneously oxidized to generate nitric acid ions and phosphoric acid ions from the nitrogen compound and the phosphorous compound respectively and the sample water is irradiated with the measuring beam so that the nitric acid ions and phosphoric acid ions can be sequentially measured in the same apparatus. Thus, it is possible to measure both a nitrogen compound and a phosphorus compound which are contained in sample water by a single apparatus.

When the sample water is heated with blow of gas containing oxygen or ozone and irradiated with ultraviolet radiation in oxidative reaction, it is possible to efficiently carry out photooxidation. The physical means of irradiating the sample water with ultraviolet radiation with blow of the gas containing oxygen or ozone requires an extremely small quantity of consumed products and hence it is not necessary to supply an oxidizer or the like. Further, the physical means is easy to operate and maintain, and analysis can continuously be made for a long time.

The oxidizing velocity is increased when a photooxidation catalyst is employed, whereby the inventive analyzer can also be expected as a total nitrogen analyzer or a total phosphorus analyzer. It is also possible to elementarily analyze nitrogen and phosphorus, and hence the inventive analyzer can also be expected as an elementary analyzer for laboratory use.

Silver halide is widely employed as a sensitive material for a photograph. Such silver halide has well-known light absorptivity of substantially absorbing the emission spectrum of a low pressure mercury lamp. However, it is not known that such silver halide has a catalytic action for oxidizing a nitrogen compound and a phosphorus compound which are contained in water.

While the function of the silver halide serving as a photooxidation catalyst is not clarified, it is known that electrons of a valence band are excited on a conducting band by light absorption to form free electrons and holes. It is conceivable that such free electrons and holes act on electrons which are bonded with nitrogen and phosphorus to cut the bonds and lead the same to oxidation.

Thus, it is possible to implement a monitor for a nitrogen compound and a phosphorus compound at a low cost in a simple structure by employing the inventive method.

An analyzer for also measuring an organic pollutant comprises a sample supply part for supplying a sample to be analyzed, an oxidative reaction unit receiving the sample from the sample supply part for oxidizing the same in a case of measuring a nitrogen compound or a phosphorus compound, a coloration reaction part for adding an ammonium molybdate solution and an L-ascorbic acid solution to the oxidized sample solution as color developers for measuring a phosphorous compound, and an absorbance measuring part for measuring absorbance of the sample solution. When sample water in which a nitrogen compound and a phosphorus compound are simultaneously oxidized by the present invention to generate nitric acid ions and phosphoric acid ions from the nitrogen compound and the phosphorus compound respectively and non-oxidized sample water are irradiated with measuring beams, it is possible to measure nitric acid ions, phosphoric acid ions and an organic pollutant in a single apparatus. Consequently, common parts are increased in the measuring apparatus for three components, whereby the analyzer is reduced in cost and simplified in structure. Further, the analyzer is easy to maintain as compared with apparatuses installed for the respective components, whereby the space therefor can be saved.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 15 is a block diagram showing a reaction part in an analyzer according to an embodiment of the present invention;

DESCRIPTION OF THE PREFERRED EMBODIMENTS

Figure 1:
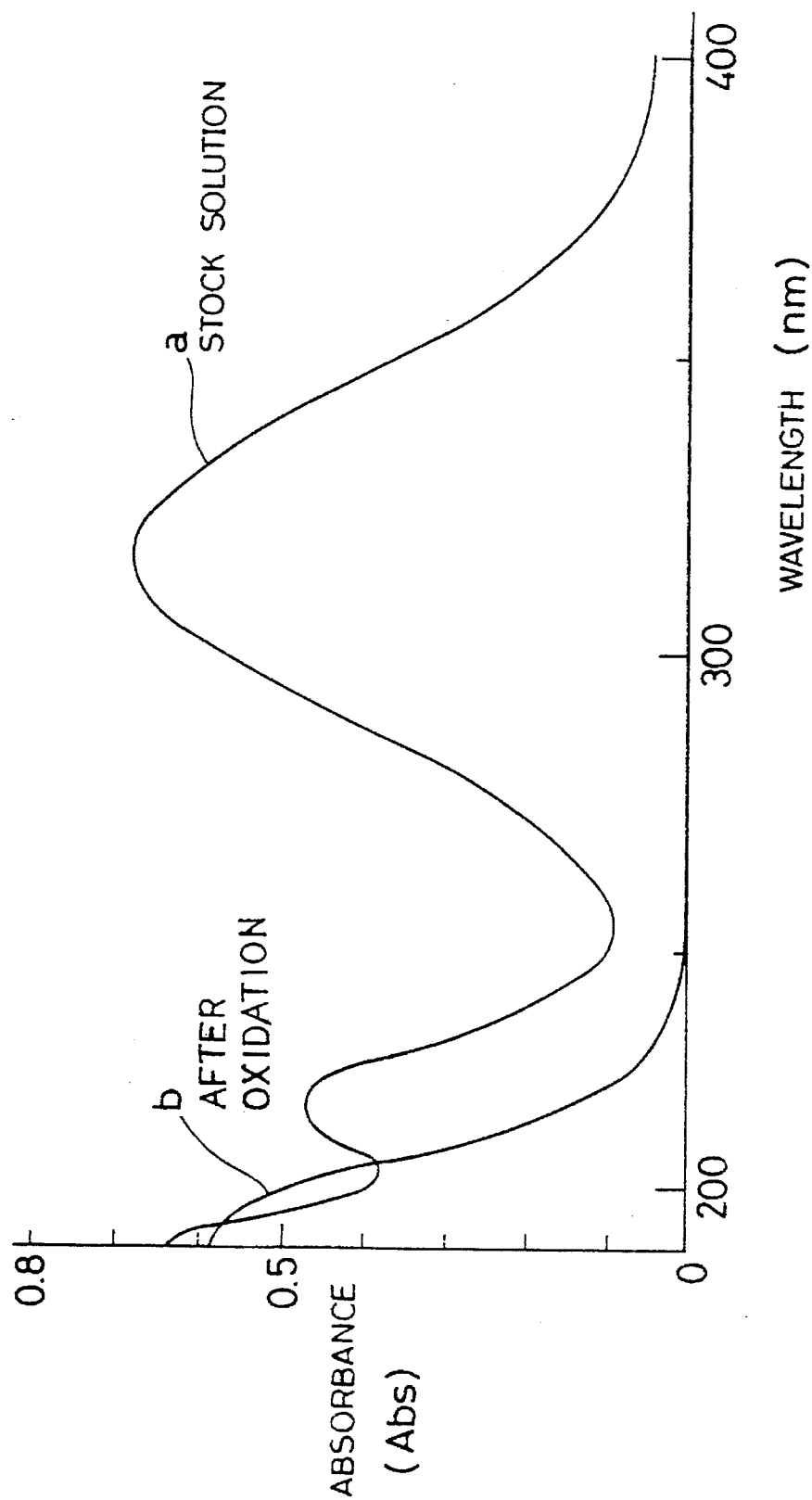
FIG. 1 illustrates absorption spectra of unsaturated organic compounds containing nitrogen before and after irradiation with ultraviolet radiation.
Figure 2:
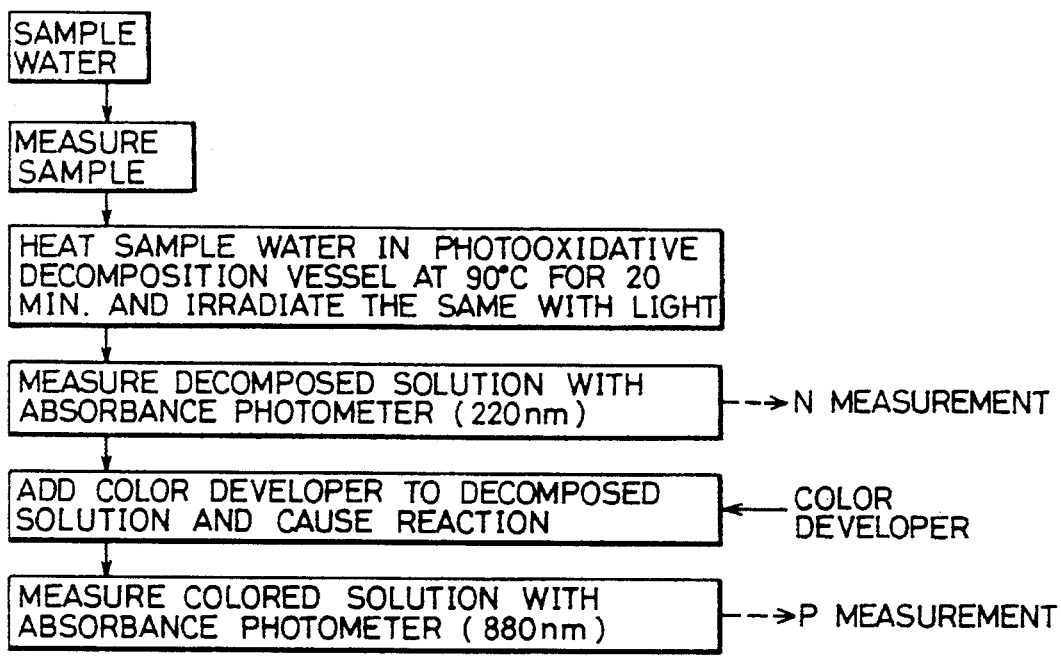
FIG. 2 is a flow chart showing an analytical method according to an embodiment of the present invention.
Figure 3:
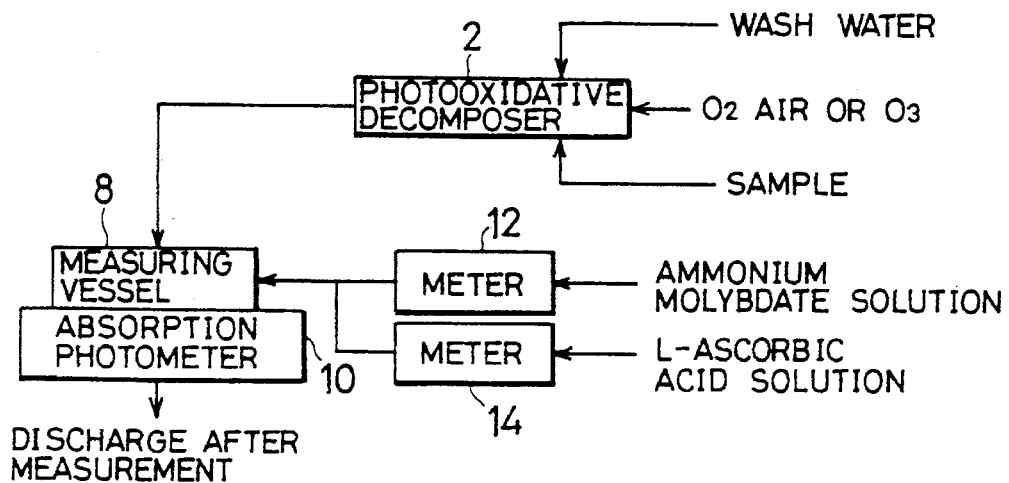
FIG. 3 is a block diagram schematically showing an exemplary apparatus implementing the inventive analytical method.
Figure 4A:
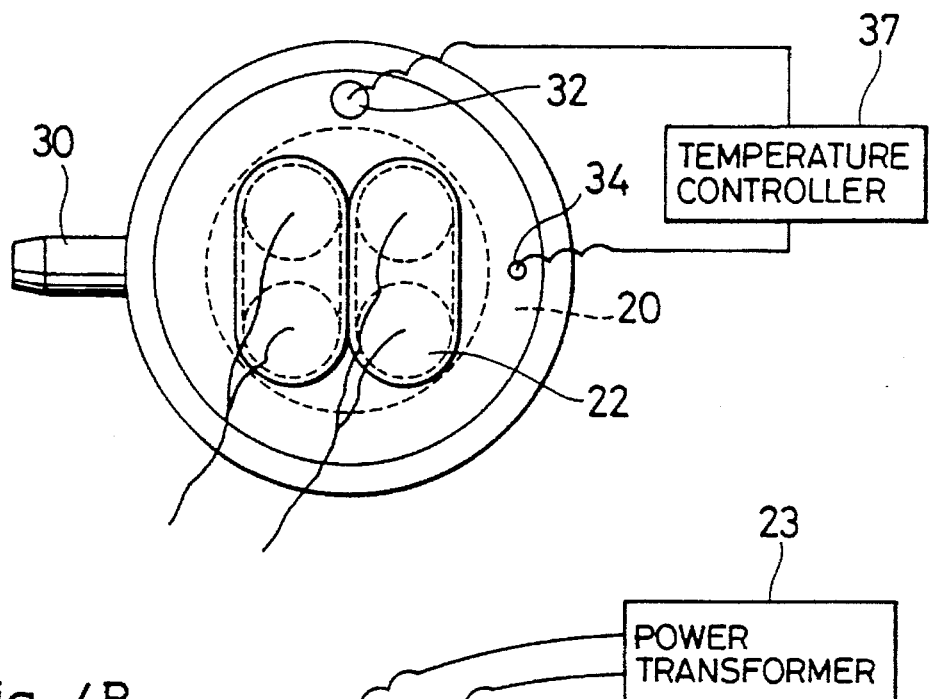
FIG. 4A is a top plan view showing an exemplary photooxidative decomposer according to the present invention.
Figure 4B:
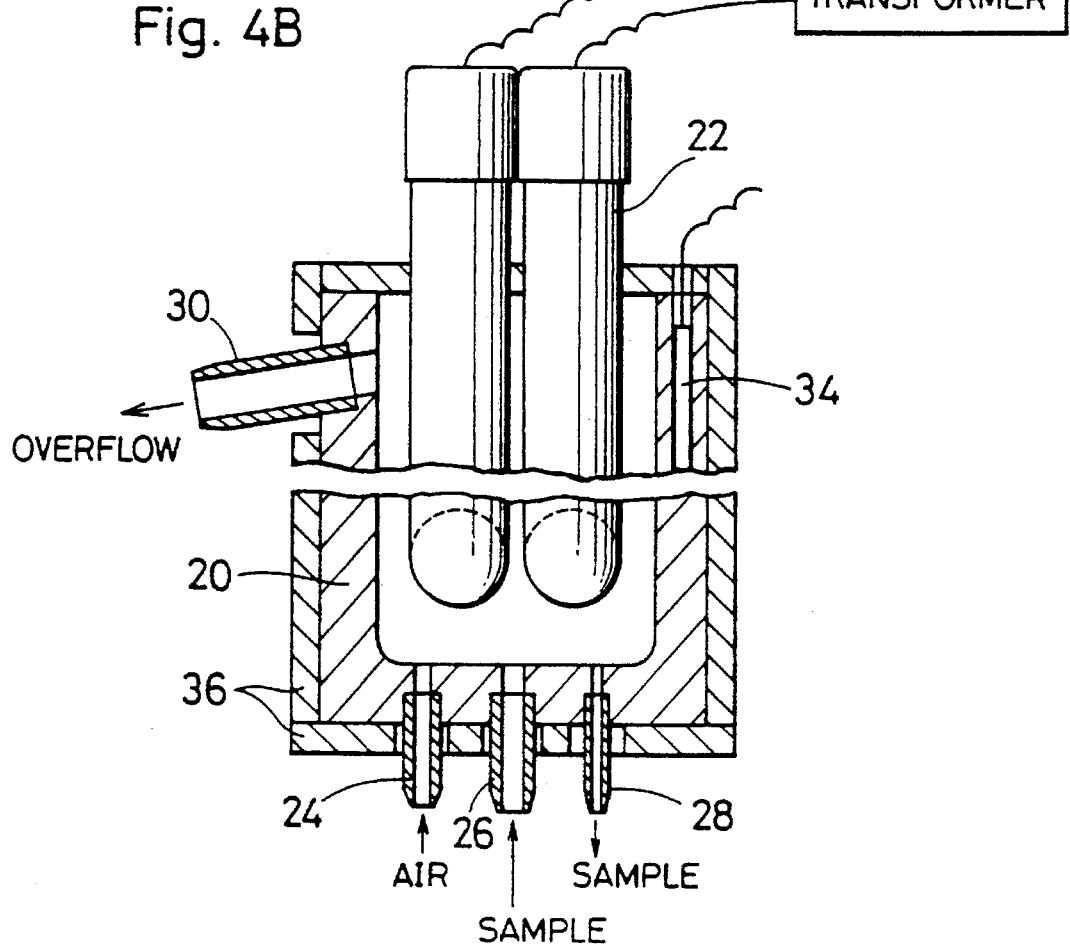
FIG. 4B is a front sectional view of the photooxidative decomposer.

FIG. 2 shows an embodiment of the present invention in order of steps, and FIG. 3 illustrates a schematic structure of a measuring apparatus. FIGS. 4A and 4B illustrate an exemplary photooxidative decomposer for carrying out photooxidative decomposition.

Referring to FIG. 3, numeral 2 denotes a photooxidative decomposer which comprises heating means to be capable of heating sample water to 50° to 100° C., as well as means for supplying oxygen or air to the sample water, and means for irradiating the sample water with ultraviolet radiation. When the photooxidative decomposer 2 employs a photooxidation catalyst, the means for supplying oxygen or air to the sample water may or may not be provided. The sample water which is irradiated with ultraviolet radiation in the photooxidative decomposer 2 so that a nitrogen compound and a phosphorus compound are oxidized into nitric acid ions and phosphoric acid ions respectively is thereafter guided to a measuring vessel 8. Numeral 10 denotes an absorption photometer for measuring absorbance of the nitric acid ions contained in the sample water in the measuring vessel 8, and a quantity of color development by the phosphoric acid ions as absorbance after addition of color developers. In order to measure the phosphoric acid ions, an ammonium molybdate solution and an L-ascorbic acid solution are measured by meters 12 and 14 respectively and mixed with each other, to be supplied to the measuring vessel 8. The photooxidative decomposer 2 and the measuring vessel 8 are supplied with wash water to be washed therewith.

FIGS. 4A and 4B illustrate an exemplary photooxidative decomposer 2. FIG. 4A is a top plan view, and FIG. 4B is a front sectional view.

FIGS. 4A and 4B show an internal cylinder type decomposer comprising a reaction vessel 20 and low pressure mercury lamps 22 for emitting ultraviolet radiation, which are provided in the reaction vessel 20 to be directly in contact with sample water. The low pressure mercury lamps 22 emit shorter-wavelength ultraviolet radiation having luminance at 185 nm, for example. The reaction vessel 20 is provided on its bottom portion with an air inlet 24, a sample water inlet 26 and a sample water outlet 28, which are provided with couplings for enabling tube connection. In order to discharge an overflow in introduction of sample water, a bypass 30 is provided on an upper portion of the reaction vessel 20. The bypass 30 is also provided with a coupling for tube connection.

A cartridge heater 32 and a temperature sensor 34 are embedded in the reaction vessel 20 which is made of aluminum, so that the reaction vessel 20 is temperature-controlled at about 90° C. The periphery of the reaction vessel 20 is covered with a heat insulating material 36 serving as a thermal insulator.

The inner surface of the reaction vessel 20 is polished into a mirror structure, for multiple reflection of the ultraviolet radiation. The material for the reaction vessel 20 is not restricted to aluminum but the same may alternatively be prepared from stainless steel or glass. The inner surface of the reaction vessel 20 is preferably polished into a mirror structure also when the same is made of stainless steel. When the reaction vessel 20 is made of Pyrex glass, on the other hand, the inner surface can be brought into a mirror structure by formation of a silver mirror or an aluminum evaporation film since the Pyrex glass does not transmit ultraviolet radiation. When the reaction vessel 20 is made of ultraviolet transmittant glass, further, a silver mirror or an aluminum evaporation film can be formed on its outer surface to provide a mirror structure. When the reaction vessel 20 is thus brought into a mirror structure, it is possible to effectively use the ultraviolet radiation, thereby improving decomposition efficiency.

The ultraviolet radiation source is not restricted to the low pressure mercury lamps 22, but may be prepared any light source such as an excimer laser, a deuterium lamp, a xenon lamp, an Hg-Zn-Pb lamp or the like, so far as the same can emit ultraviolet radiation with strong energy. However, the low pressure mercury lamp is preferable due to fitness as a monitor with a low cost and a long life. Each low pressure mercury lamp 22 is formed by an ultraviolet lamp of ultraviolet transmitting glass having a diameter of about 18 mm, which is worked into a U shape with a discharge current of 0.8 A and a discharge voltage of 10 V. When two such mercury lamps 22 are mounted on the reaction vessel 20 and dipped in the sample water, the water content in the reaction vessel 20 is about 100 ml.

Numeral 23 denotes a power transformer for turning on the low pressure mercury lamps 22, and numeral 37 denotes a temperature controller for controlling the temperature of the reaction vessel 20.

In oxidative decomposition, the low pressure mercury lamps 22 are turned on to irradiate the sample water which is stored in the reaction vessel 20 with ultraviolet radiation, while air is supplied from the air inlet 24 at about 0.1 litter/min.

This embodiment is now described with reference to a flow chart shown in FIG. 2.

The sample water, from which large soil is previously removed through a filter or the like, is supplied into the reaction vessel 20 through the sample inlet 26 while being measured. In the reaction vessel 20, the sample water is heated to 90° C. and irradiated with ultraviolet radiation by the low pressure mercury lamps 22 for 20 minutes, with supply of air from the air inlet 24. It is conceivable that oxygen atoms and ozone are generated in the sample water which is stored in the reaction vessel 20 due to such ultraviolet irradiation, to oxidize a nitrogen compound and a phosphorus compound contained in the sample water for converting the same to nitric acid ions and phosphoric acid ions respectively and cutting unsaturated bonds of an organic compound if such an organic compound is present.

After completion of photooxidative decomposition, the sample water which is stored in the reaction vessel 20 is partially or entirely taken out into the measuring vessel 8, so that the absorbance photometer 10 measures the nitric acid ions at a wavelength of 220 nm.

Then, an ammonium molybdate solution and an L-ascorbic acid solution are added to the measuring vessel 8 to color the sample water. The absorbance photometer 10 measures phosphoric acid ions contained in the as-colored solution at a wavelength of 880 nm.

Table 1 shows recovery values of nitrogen compounds and phosphorus compounds contained in standard substances, which were measured by the aforementioned method. The recovery values show rates of the nitrogen compounds and the phosphorus compounds contained in the samples, which were oxidized into nitric acid ions and phosphoric acid ions respectively. A recovery value of 100% indicates that the target nitrogen or phosphorus compound was entirely oxidized into nitric acid ions or phosphoric acid ions. Each standard substance contained nitrogen and phosphorus in concentration of 1 ppm (w/v) respectively.

TABLE 1

| Component | Recovery (%) |
|---|---|
| Nitrogen Componhd | |
| $NaNO_2$ | 103 |
| $NO_2C_6H_4OH$ | 101 |
| $NH_4Cl$ | 101 |
| $(NH_4)_2SO_4$ | 98 |
| $HOOCCH_2CH(NH_2)COOH$ | 99 |
| Phosphorus Compond | |
| $(HOCH_2)_2CHONO_2PO_3$ | 98 |
| $C_6H_5Na_2PO_4$ | 106 |
| $CH_3P(C_6H_5)_9Br$ | 94 |

It is understood from Table 1 that all recovery values were at excellent levels of about 100%.

Thus, it has been clarified possible to measure both of a nitrogen compound and a phosphorus compound by a single analyzer since both compounds are oxidized in the reaction vessel 20 and converted to nitric acid ions and phosphoric acid ions respectively.

Figure 5:
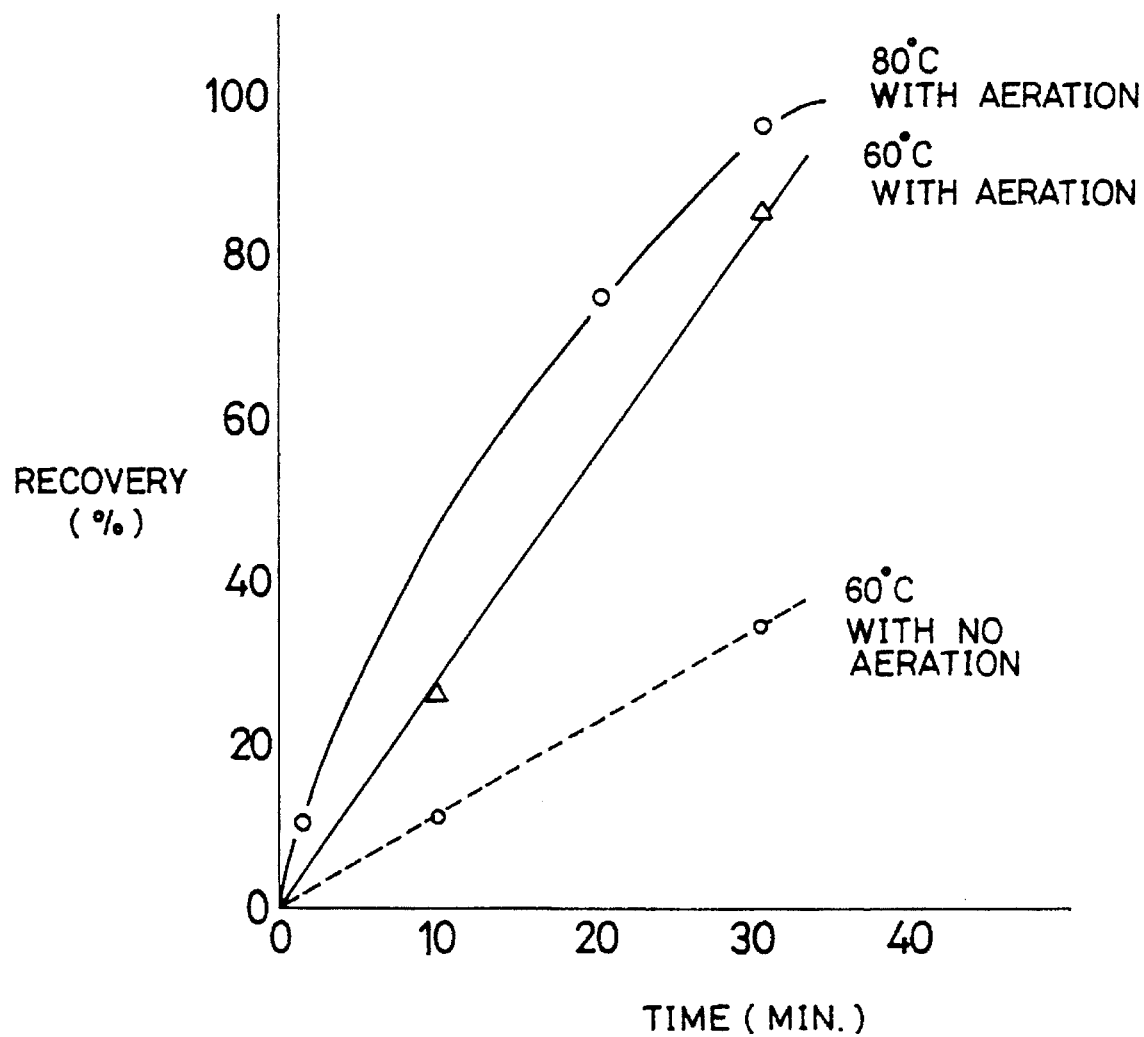
FIG. 5 illustrates measurement data showing effects of temperature and oxygen in photooxidative decomposition of a phosphorous compound.

With reference to FIG. 5, description is now made on temperature and aeration effects in ultraviolet irradiation in relation of measurement of standard samples each containing 1 ppm of methyltriphenylphosphonium bromide through the photooxidative decomposer shown in FIGS. 4A and 4B.

Comparing a case of supplying air from the air inlet 26 with a case of supplying no air with reference to samples heated to 60° C., there is difference of about three times between recovery values. Thus, it is understood that oxidation by oxygen atoms or ozone effectively functions due to supply of air in ultraviolet irradiation.

As to temperature changes with supply of air to samples in ultraviolet irradiation, difference in recovery is observed between 60° C. and 80° C. Thus, it is clearly understood that oxidative reaction is facilitated as the temperature is increased.

Figure 6:
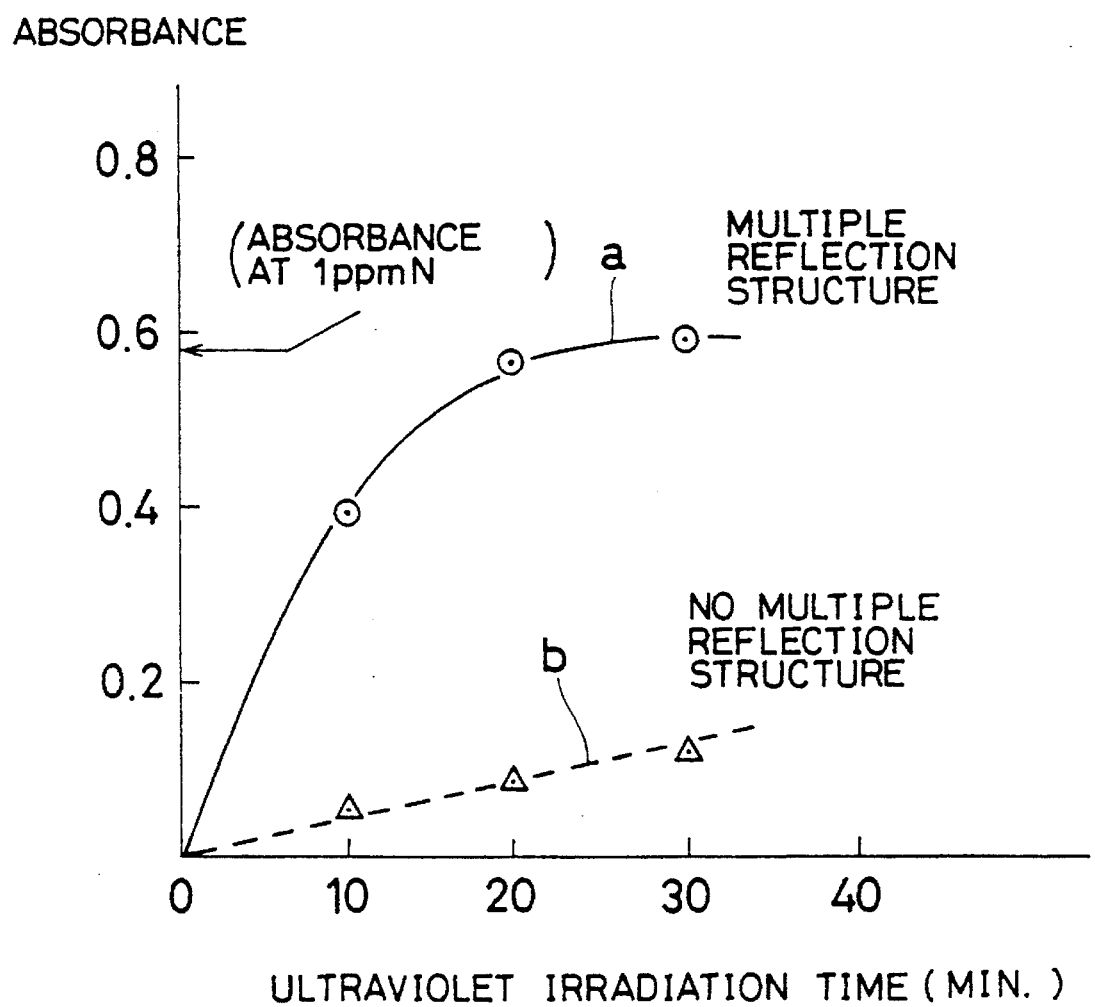
FIG. 6 illustrates measurement data showing a multiple reflection effect of ultraviolet radiation in photooxidative decomposition of a nitrogen compound.

FIG. 6 shows results of measurement of ultraviolet multiple reflection effects in a reaction vessel (a) having a mirror-finished inner surface for reflecting ultraviolet irradiation and a reaction vessel (b) having no mirror-finished inner surface. Sample water was prepared from an ammonium chloride solution containing 1 ppm of nitrogen, which was supplied at a temperature of 90° C. with supply of air at about 100 ml/min. As the result, a remarkable effect was attained in photooxidative decomposition reaction due to multiple reflection of ultraviolet radiation.

Figure 7A:
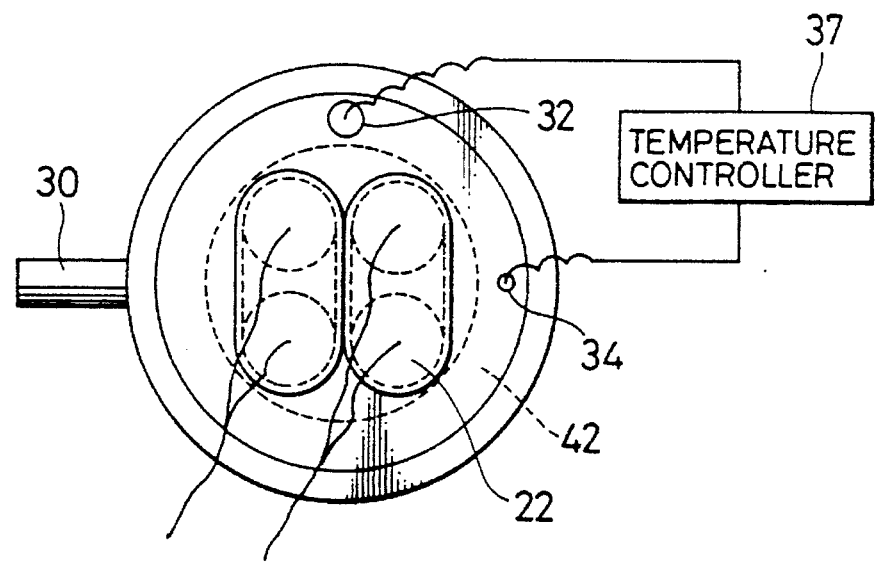
FIG. 7A is a top plan view showing another exemplary photooxidative decomposer according to the present invention.
Figure 7B:
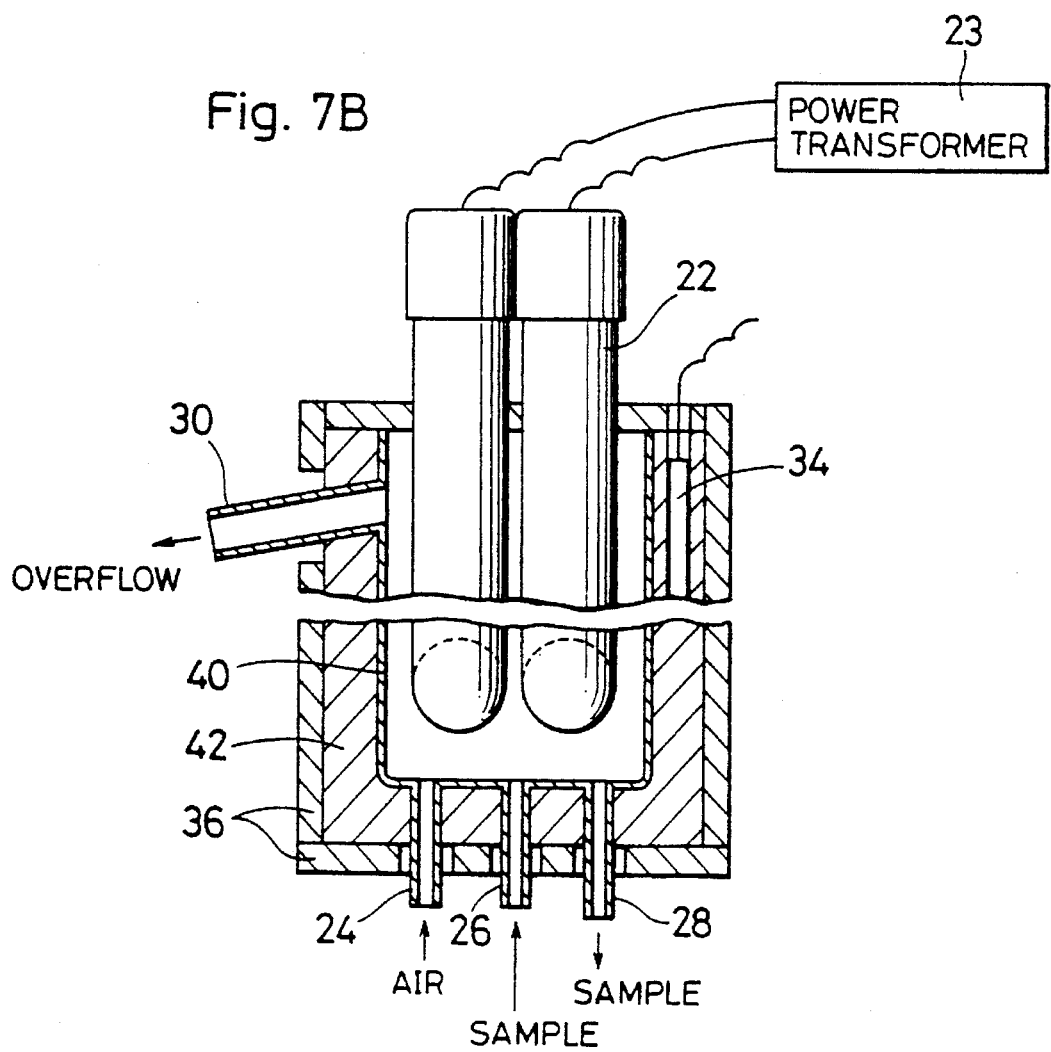
FIG. 7B is a front sectional view of the photooxidative decomposer.

The photooxidative decomposer 2 can be modified in various ways. When the sample water is prepared from sea water or saline water, the reaction vessel is preferably made of glass. FIGS. 7A and 7B show an exemplary inner cylinder type photooxidative decomposer having a reaction vessel of glass. FIG. 7A is a top plan view, and FIG. 7B is a front sectional view.

A reaction vessel 40 which is made of glass such as Pyrex is provided with an air inlet 24, a sample inlet 26 and a sample outlet 28 in its bottom portion and an overflow outlet 30 in its upper portion respectively. A protective vessel 42 of a metal having excellent heat conductivity is provided in contact with outer sides of the side and bottom portions of the reaction vessel 40, and a cartridge heater 32 and a temperature sensor 34 are embedded in the protective vessel 42. Other structures of this vessel 40 are identical to those shown in FIGS. 4A and 4B. Low pressure mercury lamps 22 are mounted in the reaction vessel 40, while the protective vessel 42 is covered with a heat insulating material 36.

In each of the photooxidative decomposers shown in FIGS. 4A and 4B and FIGS. 7A and 7B, the sample inlet 26 may be provided in the side or upper portion, in place of the bottom portion. When the sample inlet 26 is provided in the bottom portion, the same may be combined with the air inlet 24 to define a single inlet in a portion connected with the reaction vessel 20 or 40.

Figure 8A:
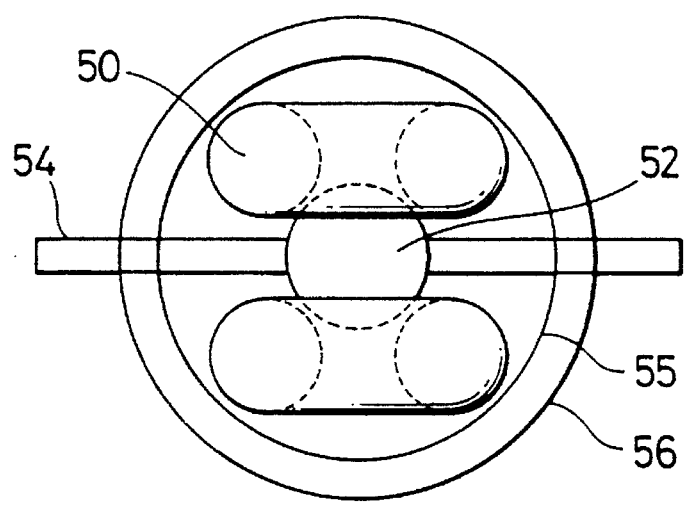
FIG. 8A is a top plan view showing still another exemplary photooxidative decomposer according to the present invention.
Figure 8B:
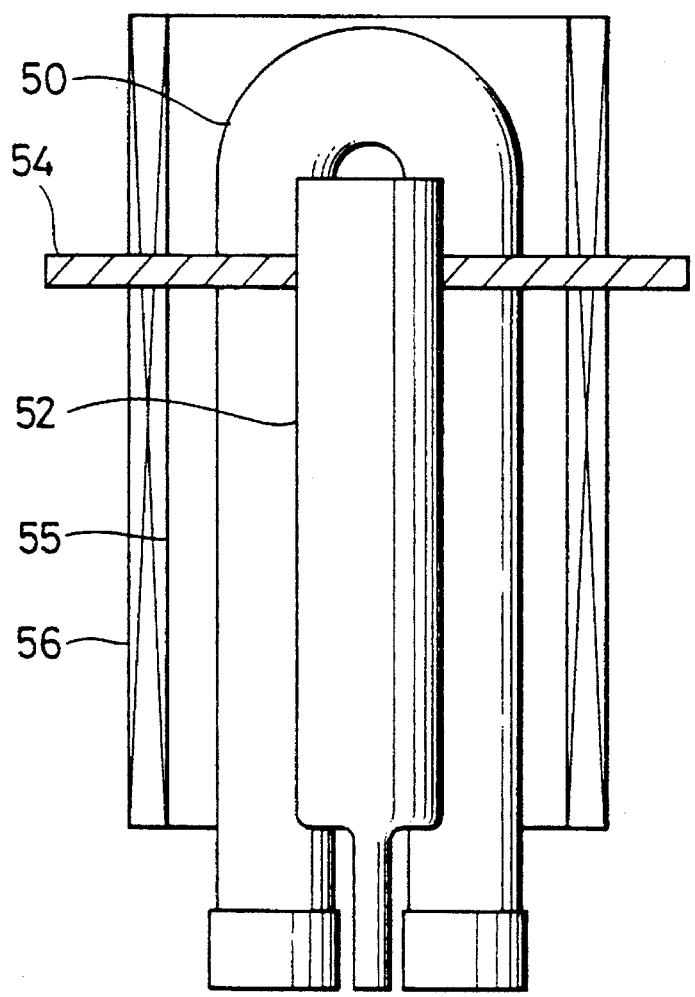
FIG. 8B is a front sectional view of the photooxidative decomposer.

FIGS. 8A and 8B show an exemplary outer cylinder type photooxidative decomposer having an ultraviolet source which is arranged outside a reaction vessel.

Referring to FIGS. 8A and 8B, two low pressure mercury lamps 50 are arranged outside a reaction vessel 52, which is made of ultraviolet transmitting glass. Numeral 54 denotes a support member for the reaction vessel 52. An air inlet, a sample inlet, a sample outlet and an overflow outlet are simply illustrated. In order to make multiple reflection of ultraviolet radiation, an outer cylinder 55 is provided outside the low pressure mercury lamps 50 for reflecting ultraviolet irradiation. Numeral 56 denotes a heater, which is provided outside the outer cylinder 55.

Comparing inner and outer cylinder type photooxidative decomposers with each other, the inner cylinder type decomposer easily causes contamination of ultraviolet lamps although the same can effectively use radiation. The outer cylinder type decomposer has reverse characteristics.

Figure 9:
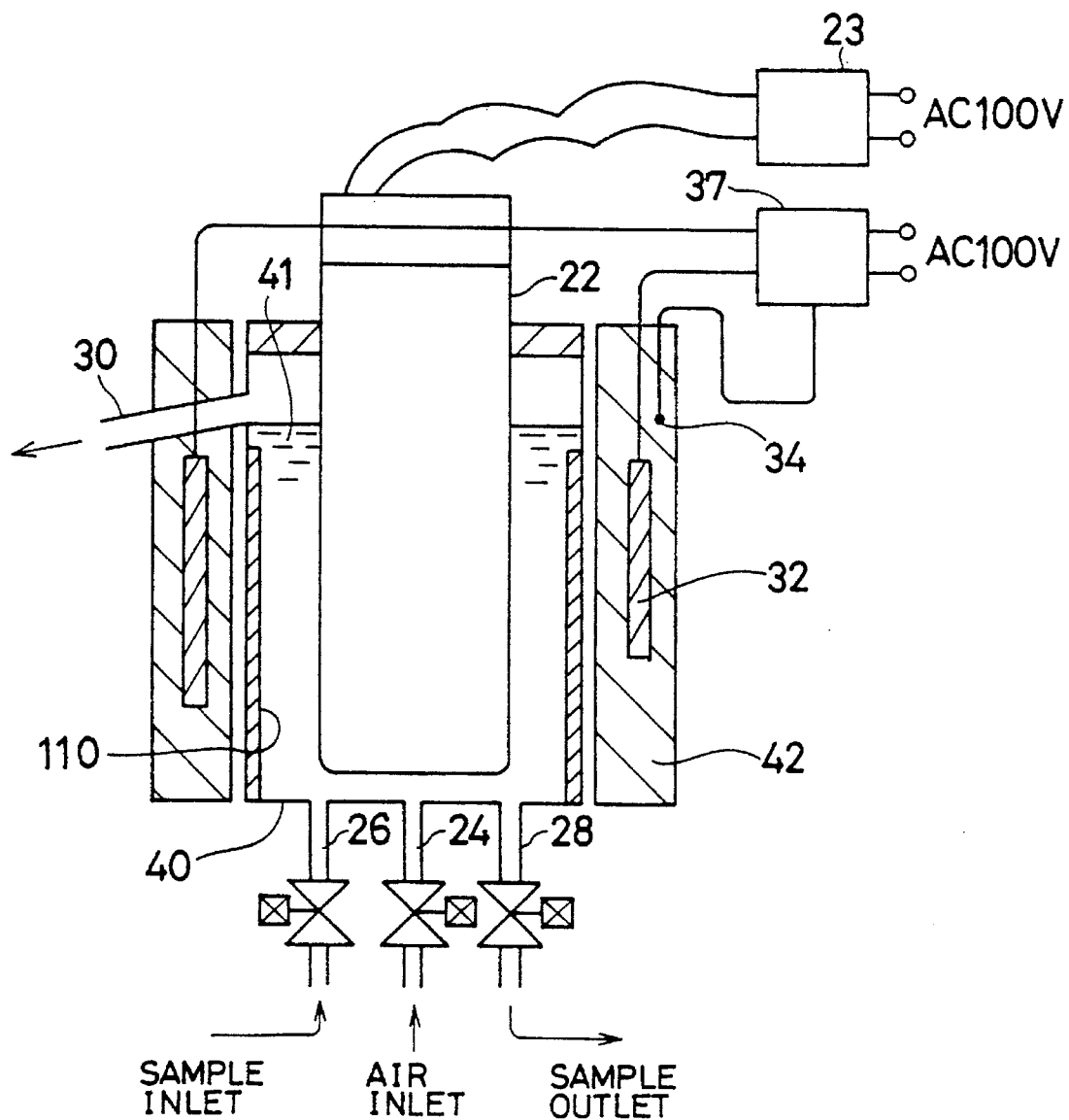
FIG. 9 is a sectional view showing a photooxidative decomposer employing a photooxidation catalyst according to an embodiment of the present invention.

FIG. 9 shows an exemplary photooxidative decomposer employing a photooxidation catalyst.

A low pressure mercury lamp 22 for serving as an ultraviolet radiation source is mounted in the interior of a reaction vessel 40 which is made of Pyrex glass. The reaction vessel 40 can store about 150 ml of sample water 41 in the state provided with the low pressure mercury lamp 22. A stabilization power source (power transformer) 23 for the low pressure mercury lamp 22 has capacity of 54 W, a lamp current of 0.6 A, a primary voltage of 100 V and a secondary voltage of 190 V. An air inlet 24 is provided in a center of a bottom portion of the reaction vessel 40, to supply air into the reaction vessel 40 at 10 ml/min. for supplying oxygen and stirring the sample water 41. A sample water inlet 26 and a sample water outlet 28 are further provided in the bottom portion of the reaction vessel 40. The air inlet 24, the sample water inlet 26 and the sample water outlet 28 are provided with switch valves respectively. A bypass 30 is provided on an upper portion of the reaction vessel 40, to discharge an overflow.

The reaction vessel 40, which is 50 mm in inner diameter, 55 mm in outer diameter and 120 mm in height, is provided therein with a photooxidation catalyst layer 110. The photooxidation catalyst layer 110 is formed by an Ag thin film having an AgCl thin film of about 50 μm in thickness on its surface, or an SiO$_2$ thin film containing TiO$_2$ having a thickness of about 2 μm, for example.

A heat sink 42 which is formed by a protective vessel of aluminum is provided in contact with the outer side of the reaction vessel 40, in order to maintain sample water stored in the reaction vessel 40 at a constant temperature within a range of 50° to 100° C. Two cartridge heaters (sheath heaters) 32 of about 30 W are embedded in the heat sink 42, while a temperature sensor 34 which is formed by a thermocouple is also embedded therein. A temperature controller 37 is set to adjust the temperature of the sample water at 90° C., for example. The temperature of the sample water is abruptly increased to 90° C. by heat from the heat sink 42 and that generated in the low pressure mercury lamp 22.

The ultraviolet radiation source is not restricted to the low pressure mercury lamp 22, but may alternatively be prepared from a light source such as an excimer laser, a deuterium lamp, a xenon lamp, an Hg-Zn-Pb lamp or the like, so far as the same can emit ultraviolet radiation with strong energy.

In oxidative decomposition, the low pressure mercury lamp 22 is turned on to irradiate the sample water which is stored in the reaction vessel 40 with ultraviolet radiation, while air is supplied from the air inlet 24.

The decomposer shown in FIG. 9 is similar in operation to that shown in FIGS. 4A and 4B, with addition of action of the photooxidation catalyst.

Figure 10:
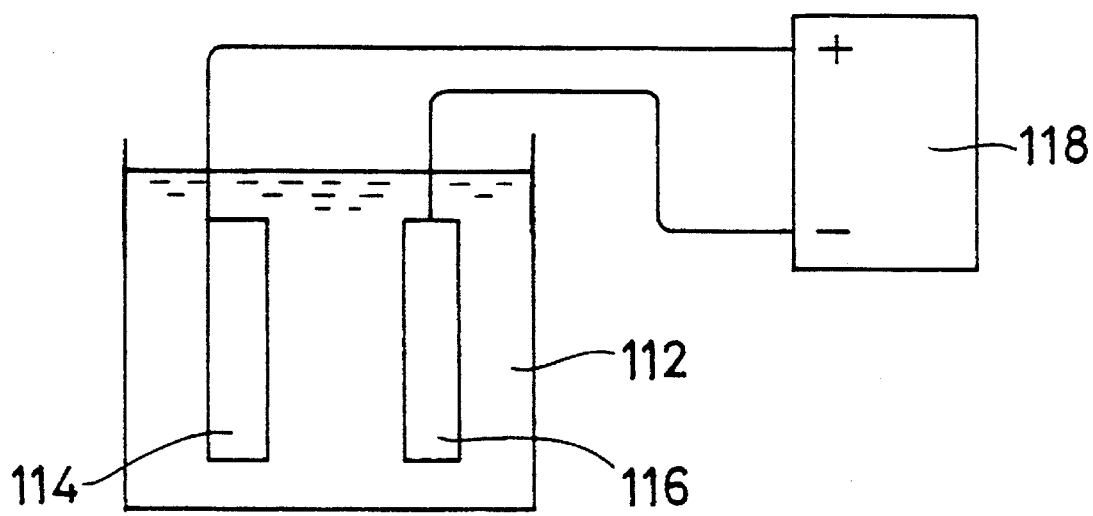
FIG. 10 schematically illustrates a method of preparing the photooxidation catalyst employed in the embodiment shown in FIG. 9.

FIG. 10 illustrates a method of forming an AgCl thin film, serving as an example of the photooxidation catalyst layer 110 shown in FIG. 9. An Ag thin plate 114 serving as a main material for forming a photooxidation catalyst is dipped as an anode in an NaCl solution 112 of about 1 mol, and a Pt thin plate 116 serving as a counter electrode is set to have the same surface area as the Ag thin plate 114. When a voltage of about 0.3 V is applied from a dc power source 118 across the electrodes 114 and 116, the surface of the AgCl thin plate 114 is sufficiently plated in about 30 minutes, to form an AgCl thin film.

An AgI thin film or an AgBr thin film can be prepared from an NaI solution or an NaBr solution similarly to the above.

In place of the Ag thin plate having an AgCl thin film which is set on the inner side of the reaction vessel 40 as shown in FIG. 9, an Ag thin film may be formed on the inner surface of the reaction vessel 40 by silver mirror reaction so that the Ag thin film is electrolyzed in an NaCl solution similarly to FIG. 10, thereby forming an AgCl thin film. Alternatively, a coating of silver paste may be formed on the inner surface of the reaction vessel 40, to form an AgCl thin film similarly to the above.

Figure 11:
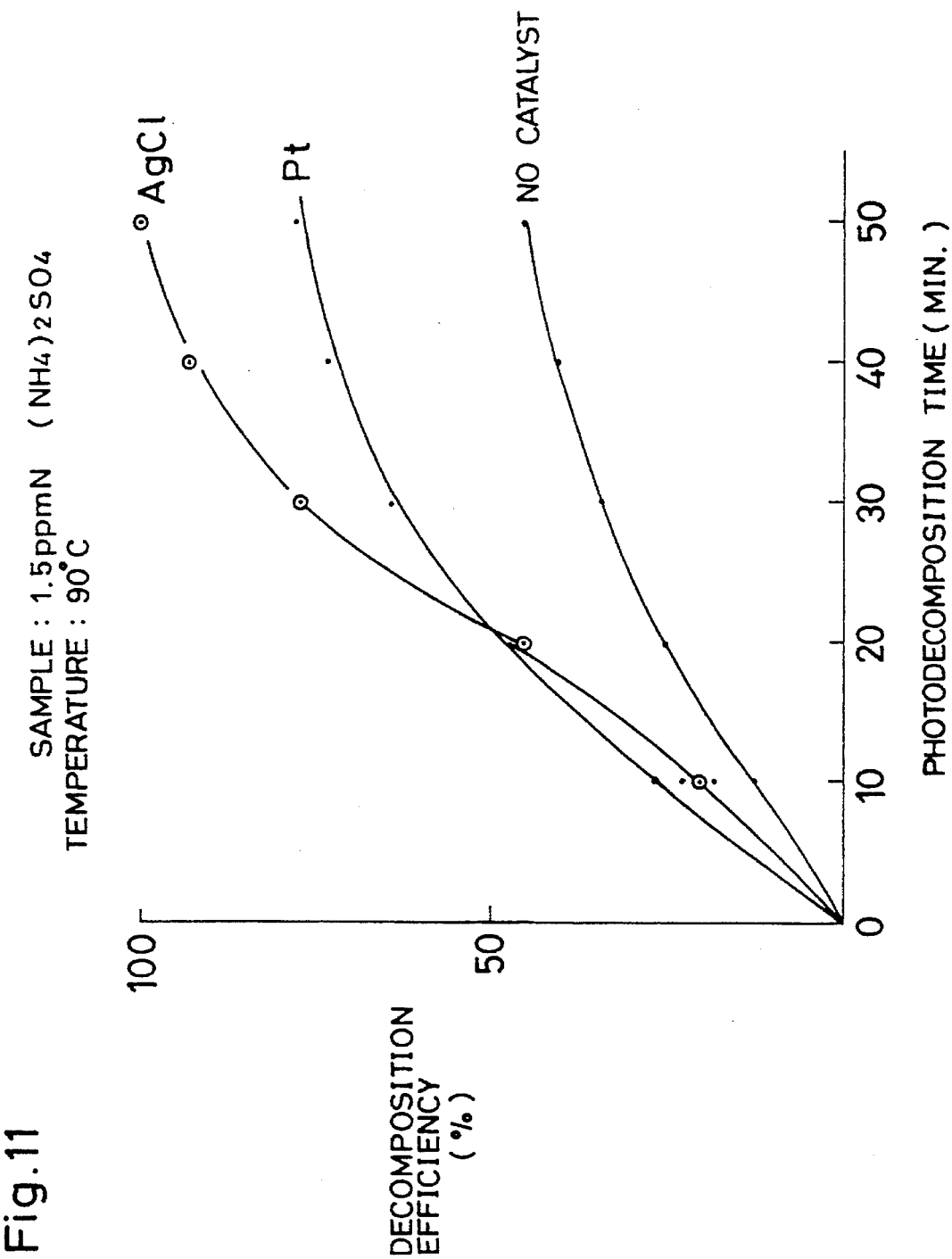
FIG. 11 illustrates photooxidative decomposition velocities in cases of employing and not employing the photooxidation catalyst.

FIG. 11 shows decomposition efficiency attained by a photooxidation catalyst of AgCl in comparison with those of other methods. A gas containing oxygen or ozone was not blown. The curve "AgCl" shows the result of investigation on sample water of 1.5 ppmN in concentration (concentration of 1.5 ppm in terms of nitrogen) with employment of (NH$_4$)$_2$SO$_4$ as a typical example of hardly decomposable nitrogen compound in ammonium state through the photooxidative decomposer shown in FIG. 9. The curve "Pt" shows a case of employing a Pt thin film as a photooxidation catalyst, and a curve "NO CATALYST" shows a case of employing no photooxidation catalyst. It is understood from FIG. 11 that a remarkable catalytic effect was attained when AgCl was employed as the photooxidation catalyst. While Pt is known as an oxidation catalyst, FIG. 11 shows that the same has lower catalytic activity than AgCl in oxidation of a nitrogen compound and a phosphorus compound.

As to an embodiment of employing TiO$_2$ as a photooxidation catalyst, a method of forming an SiO$_2$ thin film containing TiO$_2$ in the interior of the reaction vessel 40 is now described.

First Method

A mixture containing the following components is prepared:

| | |
|---|---|
| Si(OC$_2$H$_5$)$_4$ | 5.4 ml |
| C$_2$H$_5$OH | 50 ml |
| 1N—HCl | 20 ml |
| H$_2$O | 1.7 ml |
| 2% hydroxypropyl cellulose | 5 ml |

These components are homogeneously mixed with each other to form a sol, and 1 g of anatase TiO$_2$ powder is added to and mixed with the mixed sol. This sol is applied to the inner surface of the reaction vessel 40, and dried at 100° C. to be gelated. Thereafter the as-formed gel is fired at 700° C. for 3 hours, whereby an SiO$_2$ thin film containing TiO$_2$ is formed on the inner surface of the reaction vessel 40 with a thickness of about 2 μm.

Second Method

A mixture containing the following components is prepared:

| | |
|---|---|
| Si(OC$_2$H$_5$)$_4$ | 5.4 ml |
| C$_2$H$_5$OH | 50 ml |
| 1N—HCl | 20 ml |
| H$_2$O | 1 ml |
| tetraisopropyl titanate (Ti(OC$_3$H$_7$)$_4$) | 5 ml |

This mixture is homogenized and applied to the inner surface of the reaction vessel, dried at 100° C. to be gelated, and thereafter fired at 400° C. for 3 hours. Thus, a TiO$_2$·SiO$_2$ thin film of about 2 μm in thickness is formed on the inner surface of the reaction vessel.

Third Method

A mixture containing the following components is prepared:

| | |
|---|---|
| Si(OC$_2$H$_5$)$_4$ | 5.4 ml |
| C$_2$H$_5$OH | 50 ml |
| 1N—HCl | 20 ml |
| H$_2$O | 1.7 ml |
| 2% hydroxypropyl cellulose | 5 ml |
| chloroplatinic acid | 100 mg |

These components are homogeneously mixed with each other to form a sol, and 1 g of anatase TiO$_2$ powder is added to and mixed with the mixed sol. This sol is applied to the inner surface of the reaction vessel 40, and dried at 100° C. to be gelated. Thereafter the as-formed gel is fired at 700° C. for 3 hours, whereby an SiO$_2$ thin film containing TiO$_2$ is formed on the inner surface of the reaction vessel 40 with a thickness of about 2 μm.

Fourth Method

A mixture containing the following components is prepared:

| | |
|---|---|
| Si(OC$_2$H$_5$)$_4$ | 5.4 ml |
| C$_2$H$_5$OH | 50 ml |
| 1N—HCl | 20 ml |
| H$_2$O | 1.7 ml |
| 2% hydroxypropyl cellulose | 5 ml |
| chloroplatinic acid | 100 mg |
| RuO$_2$ | 25 mg |

These components are homogeneously mixed with each other to form a sol, and 1 g of anatase $TiO_2$ powder is added to and mixed with the mixed sol. This sol is applied to the inner surface of the reaction vessel 40, and dried at 100° C. to be gelated. Thereafter the as-formed gel is fired at 700° C. for 3 hours, whereby an $SiO_2$ thin film containing $TiO_2$ is formed on the inner surface of the reaction vessel 40 with a thickness of about 2 μm.

An $SiO_2$ thin film containing $TiO_2$ was formed on the inner surface of a reaction vessel of a photooxidative decomposer corresponding to that shown in FIG. 9 by the first method, and interfering substances of $Br^-$ and $Cl^-$ were added to a sample solution containing 1 ppmN of $(NH_4)_2SO_4$. 100 ppm of $Br^-$ was added in the form of $NaBr^-$, and 2 percent by weight of $Cl^-$ was added in the form of NaCl. The sample conditions were set on the assumption of a case of measuring sea water as sample water, for confirming influences exerted by $Br^-$ and $Cl^-$ on the sea water. Table 2 shows results on photooxidation catalysts prepared from $TiO_2$ according to the present invention and from platinum as comparative example.

TABLE 2

| Photooxidation | Interfering Substance | |
| --- | --- | --- |
| Catalyst | NaBr | NaCl |
| TiO | 0.93 ppmN | 0.73 ppmN |
| Pt | 0.56 ppmN | 0.66 ppmN |

While oxidation efficiency was reduced to 0.56 ppmN in the comparative sample employing Pt as the photooxidation catalyst due to interference by $Br^-$, that in the inventive sample employing $TiO_2$ was reduced only to 0.93 ppmN. Also as to influence by $Cl^-$, oxidation efficiency was reduced to 0.66 ppmN in the case of Pt while that in the inventive sample employing $TiO_2$ was reduced only to 0.73 ppmN. Thus, it is understood that the interference by $Br^-$ and $Cl^-$ in nitrogen compound oxidation is reduced when $TiO_2$ is employed as the photooxidation catalyst according to the present invention.

When sea water is analyzed as sample water, bromine ions etc. contained in the sea water may serve as interference substances to reduce oxidation efficiency for a nitrogen compound and a phosphorus compound. When $TiO_2$ is employed as the photooxidation catalyst, however, it is possible to implement an analyzer which is also suitable for analyzing sea water.

Table 3 shows results of measurement of decomposition efficiency of $TiO_2$ photooxidation catalysts. Every catalyst attained excellent decomposition efficiency.

TABLE 3

| Photooxidation Catalyst (Method) | Decomposition Efficiency at 1 ppmN-$(NH_4)_2SO_4$ |
| --- | --- |
| $TiO_2$ (First method) | 0.99 |
| $TiO_2$ + Pt (Second method) | 0.99 |
| $TiO_2$ + Pt + $RuO_2$ (Fouth method) | 0.93 |

When such a photooxidation catalyst is employed, it is not requisite to blow gas containing oxygen or ozone into the sample water which is irradiated with ultraviolet radiation.

Figure 12A:
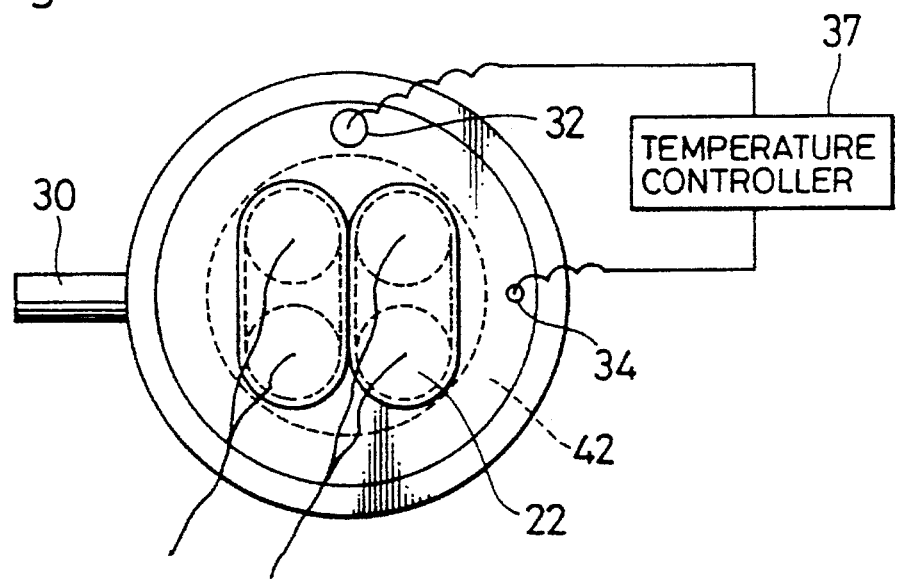
FIG. 12A is a plan view showing a batch type photooxidative decomposer employing a photooxidation catalyst according to another embodiment of the present invention.
Figure 12B:
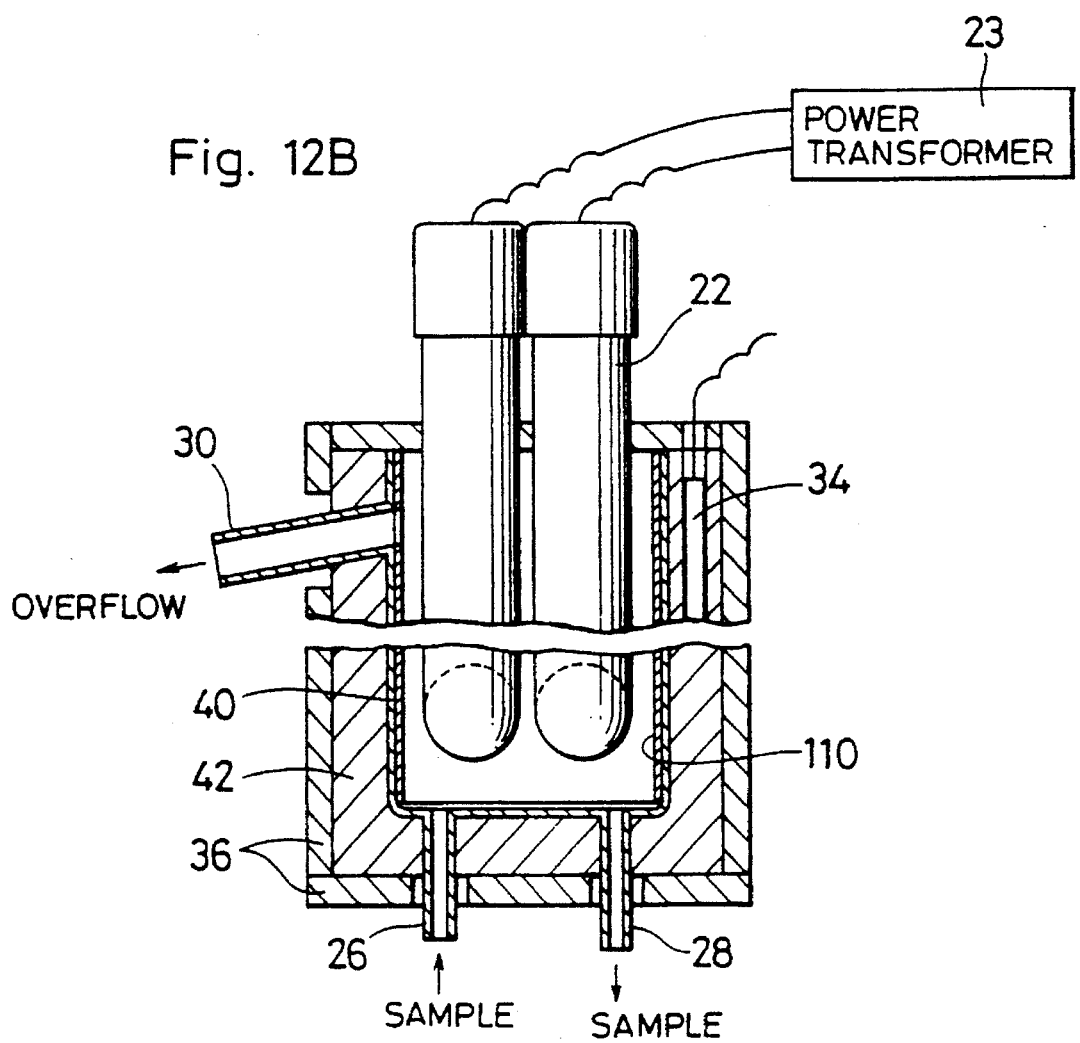
FIG. 12B is a front sectional view of the photooxidative decomposer.

FIGS. 12A and 12B show an exemplary photooxidative decomposer for irradiating sample water with ultraviolet radiation while not employing such oxidative gas. FIG. 12A is a top plan view, and FIG. 12B is a front sectional view. Low pressure mercury lamps 22 for emitting ultraviolet radiation are provided in a reaction vessel 40 which is made of glass such as Pyrex, to be directly in contact with sample water in the reaction vessel 40. The low pressure mercury lamps 22 emit ultraviolet radiation of a shorter wavelength having luminance at 185 nm, for example. A sample inlet 26 and a sample outlet 28 are provided in a bottom portion of the reaction vessel 40. A bypass 30 is provided on an upper portion of the reaction vessel 40, to discharge an overflow upon introduction of the sample water. A photooxidation catalyst 110 of AgCl or $TiO_2$ is provided on an inner wall surface of the reaction vessel 40, to be capable of being in contact with the sample water. A heat sink 42 of a heat conductive metal protective vessel is provided in contact with the outer sides of the reaction vessel 40 on side and bottom portions of the reaction vessel 40, while a cartridge heater 32 and a temperature sensor 34 are embedded in the heat sink 42. The outer side of the heat sink 42 is covered with a heat insulating material 36.

In the aforementioned photooxidative decomposer, the sample inlet 26 provided in the bottom portion may alternatively be provided in the side or upper portion. When the sample inlet 26 is provided in the bottom portion and an air inlet is provided, the sample inlet 26 may be combined with the air inlet to define a single inlet in a portion connected with the reaction vessel 40.

Figure 13:
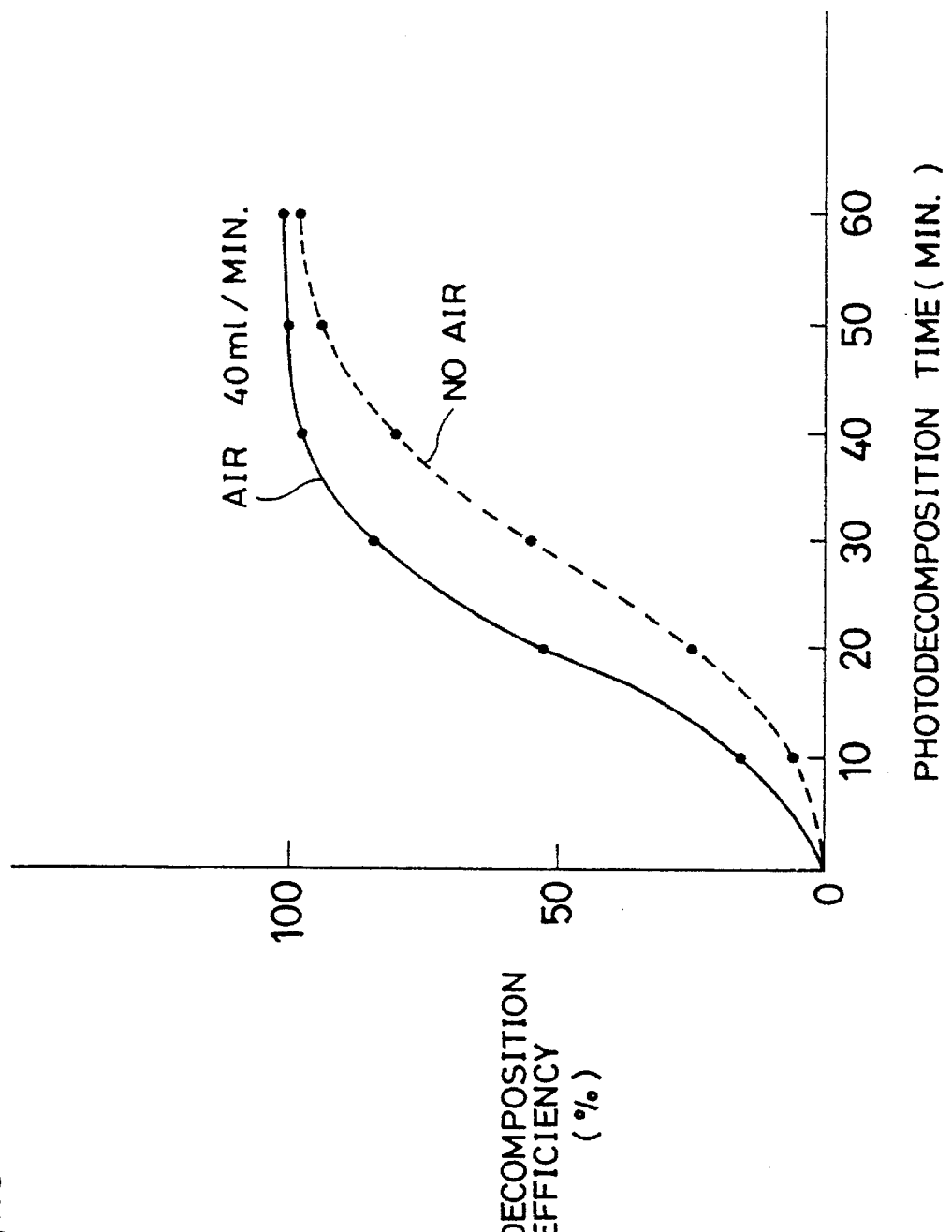
FIG. 13 illustrates measurement data showing an effect of oxygen in photooxidative decomposition of a nitrogen compound.

FIG. 13 illustrates difference in oxidation efficiency between a case of blowing air into sample water and a case of not blowing air in ultraviolet irradiation. While higher oxidation efficiency is attained in the case of blowing air, high oxidation efficiency is also attained in the case of not blowing air due to an effect of a photooxidation catalyst. Thus, it is understood possible to attain sufficient oxidation efficiency without blowing oxidative gas such as air, by increasing a contact area between an oxidation catalyst and sample water.

Oxidation efficiency for a nitrogen compound and a phosphorus compound is improved by applying ultraviolet radiation under presence of a photooxidation catalyst, whereby it is also possible to form a flow-type photooxidative decomposer for oxidizing sample water while continuously feeding the same.

FIGS. 14A to 14D show exemplary flow-type photooxidative decomposers.

Figure 14A:
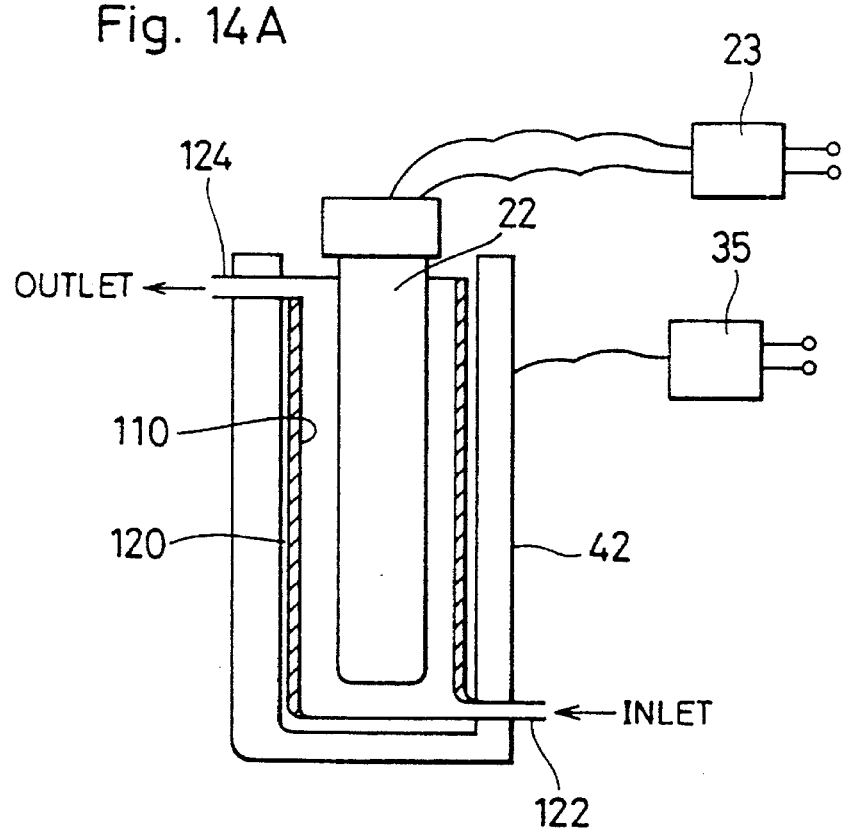
FIG. 14A is a sectional view showing a first example of a flow-type photooxidative decomposer.

In the photooxidative decomposer shown in FIG. 14A, a photooxidation catalyst 110 of an AgCl thin film or a $TiO_2$ thin film is provided in the interior of a reaction vessel 120, to be in contact with sample water. A sample water inlet 122 and an outlet 124 are provided in a bottom portion and an upper end of the reaction vessel 120 respectively. A low pressure mercury lamp 22 is mounted in the reaction vessel 120, and turned on by a stabilizing power source 23. A heat sink 42 having a heater and a temperature sensor is provided outside the reaction vessel 120.

Figure 14B:
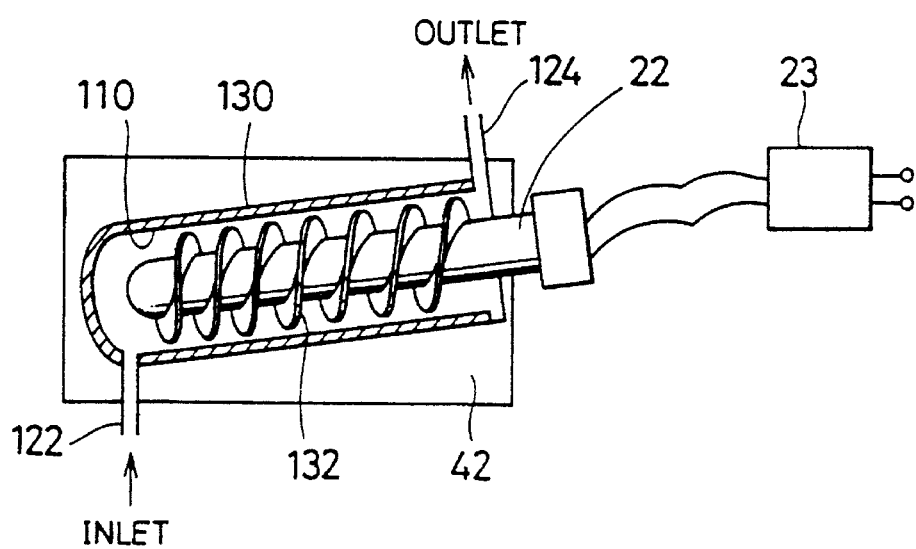
FIG. 14B is a sectional view showing a second example of a flow-type photooxidative decomposer.

In the photooxidative decomposer shown in FIG. 14B, a reaction vessel 130 provided with a photooxidation catalyst 110 on its inner surface is obliquely set while a sample water inlet 122 and an outlet 124 are provided in a bottom portion and an upper end thereof respectively. A low pressure mercury lamp 22 is mounted on a central portion of the reaction vessel 130 and a spiral plate 132 is provided between the low pressure mercury lamp 22 and the reaction vessel 130, so that sample water which is supplied from the inlet 122 is guided to the outlet 124 along the spiral plate 132 through the low pressure mercury lamp 22. A heat sink 42 having a heater and a temperature sensor is provided outside the reaction vessel 120.

Figure 14C:
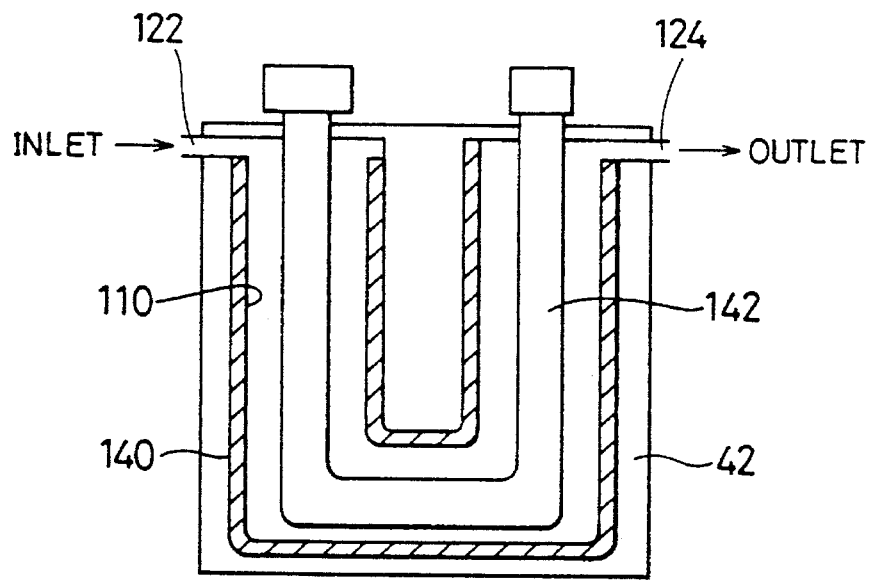
FIG. 14C is a sectional view showing a third example of a flow-type photooxidative decomposer.

In the photooxidative decomposer shown in FIG. 14C, a reaction vessel 140 provided with a photooxidation catalyst 110 on its inner surface has a U-shaped section, while a sample water inlet 122 and an outlet 124 are provided in a bottom portion and an upper end thereof respectively. A U-shaped low pressure mercury lamp 142 is mounted on the interior of the reaction vessel 140 along its U-shaped section. A heat sink 42 having a heater and a temperature sensor is provided outside the reaction vessel 140.

Figure 14D:
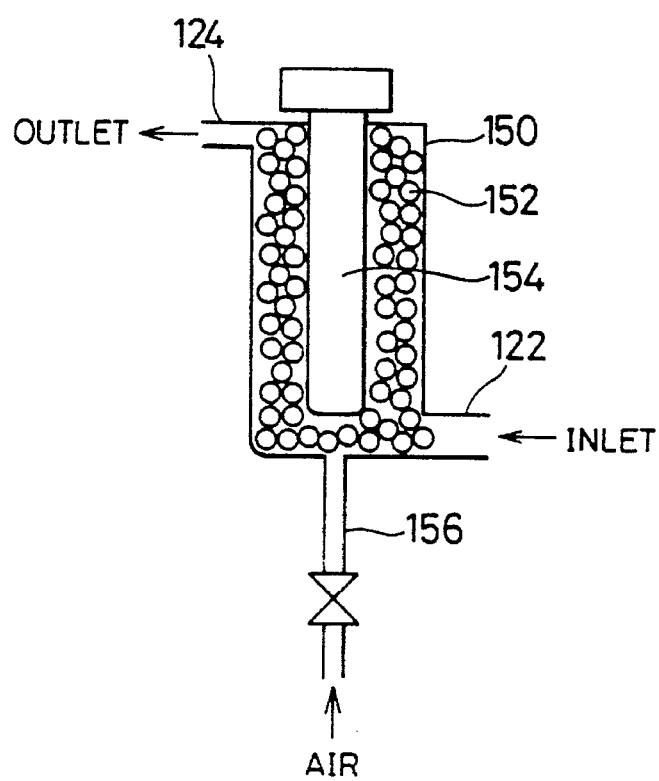
FIG. 14D is a sectional view showing a fourth example of a flow-type photooxidative decomposer.

The photooxidative decomposer shown in FIG. 14D is different from those shown in FIGS. 14A to 14C in a point that a catalyst is not formed by a thin film, but prepared from AgCl particles 152. A sample water inlet 122 and an outlet 124 are provided in a bottom portion and an upper end of the reaction vessel 150 respectively.

A low pressure mercury lamp 154 is mounted on a central portion of the reaction vessel 150, and the AgCl particles 152 are charged between the low pressure mercury lamp 154 and the reaction vessel 150. An air inlet 156 is provided in a central portion of the bottom portion of the reaction vessel 150, to be capable of supplying air into the reaction vessel 150 in ultraviolet irradiation. The AgCl particles 154 are prepared by coating surfaces of spheres of glass or alumina with Ag to convert the same to AgCl, or coating such spheres with AgCl thin films, for example.

Referring to FIG. 14D, light from the low pressure mercury lamp 154 is interfered by the AgCl particles 154 serving as the catalyst, and hence air is supplied to stir the sample water.

In each of the photooxidative decomposers shown in FIGS. 14A to 14D, it is necessary to adjust the flow rate of the sample water to approach decomposition efficiency for a nitrogen compound and a phosphorus compound to 100%, while it is not necessarily required to increase the reaction vessel in capacity.

Figure 16:
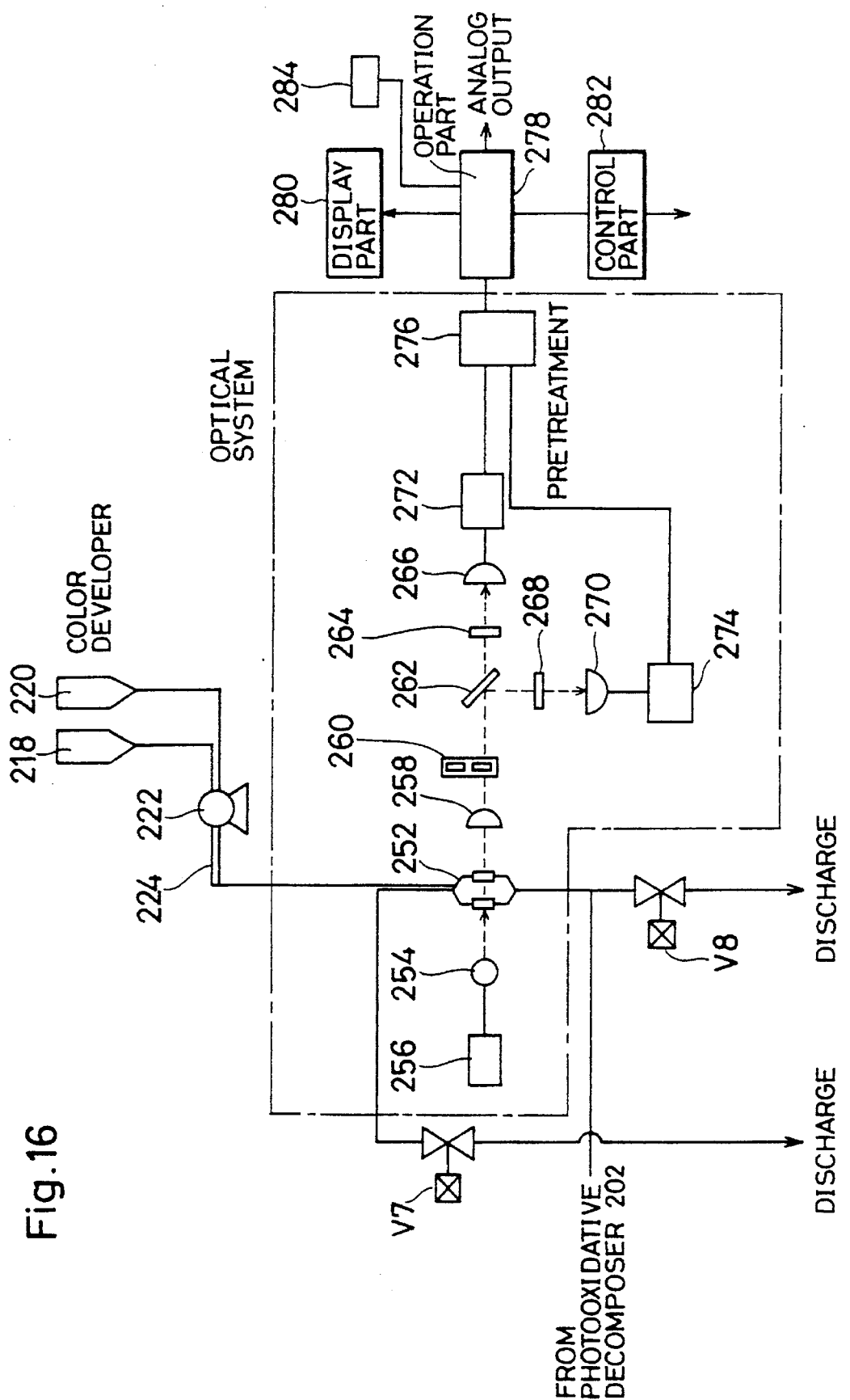
FIG. 16 is a block diagram showing a measuring part in the analyzer shown in FIG. 15.

FIGS. 15 and 16 show an exemplary analyzer for a nitrogen compound and a phosphorus compound, which is formed by a batch type photooxidative decomposer. FIG. 15 shows a reaction part, and FIG. 16 shows a measuring part.

Numeral 202 denotes a photooxidative decomposer for oxidizing a nitrogen compound and a phosphorus compound into nitric acid ions and phosphoric acid ions respectively by ultraviolet irradiation, which may be or may not be provided with a photooxidation catalyst on its inner surface. A supply pipe 206 for supplying sample water, air and clean wash water and a takeout pipe 208 for taking out sample water after oxidative reaction are connected to a bottom portion of an oxidative reaction vessel 204 of the photooxidative decomposer 202, while a discharge pipe 210 for discharging an overflow of the sample water, the wash water and air and a calibration solution supply pipe 216 for supplying a calibration solution 212 through a valve 214 are connected to an upper portion of the oxidative reaction vessel 204. The discharge pipe 210 is connected with a discharge valve V5, so that the sample water and the like are discharged through this valve V5.

A low pressure mercury lamp 226 for emitting ultraviolet radiation of a shorter wavelength having luminance at 185 nm, for example, is arranged in the oxidative reaction vessel 204 as a light source for photooxidative decomposition. In oxidative decomposition, the low pressure mercury lamp 226 is turned on by a power source 228, to irradiate the sample water which is stored in the oxidative reaction vessel 204 with ultraviolet radiation.

A heater 230 is provided in the oxidative reaction vessel 204 for maintaining the sample water which is stored therein at a prescribed temperature of 50° to 100° C. The sample water can be controlled at the prescribed temperature by a temperature controller through a temperature sensor 232. The sample water stored in the oxidative reaction vessel 204 is temperature-controlled to 90° C., for example. The heater 230 may be embedded in the oxidative reaction vessel 204 as a cartridge heater with the temperature sensor 232. The outer side of the oxidative reaction vessel 204 may be covered with a heat insulating material at need.

A sample water passage is connected through a valve 234 and a pinch valve V3, in order to supply the sample water through the supply pipe 206 which is provided on the lower portion of the oxidative reaction vessel 204. A passage for discharging the sample water through a valve V4 is connected to the passage between the valves 234 and V3.

An air supply passage is connected to the supply pipe 206 through a filter 238, a pump 240, a needled flow meter 242 and a valve V1, in order to supply air for aerating the sample water in oxidative reaction.

Further, a clean water supply passage is connected to the supply pipe 206 through a ball valve 244, an electromagnetic valve V2, a demineralizer 246 and a check valve 248, to supply clean water for washing passages of the oxidative reaction vessel 204, a measuring cell and the like.

A discharge valve 250 is connected to the supply pipe 206, so that liquids remaining in the oxidative reaction vessel 204 and the supply pipe 206 can be discharged through this valve 250.

The takeout pipe 208 which is provided on the bottom portion of the oxidative reaction vessel 204 is connected to a bottom portion of an absorbance measuring cell 252 through a valve V6. The absorbance measuring cell 252 can discharge water from its bottom portion through a valve V8, and a discharge pipe having a valve V7 is connected to its upper portion for discharging an overflow of the sample water and the wash water.

The absorbance measuring cell 252 can make the sample water flow, and comprises a transmission window of quartz glass for transmitting measuring beams over ultraviolet and near infrared regions. A xenon flash lamp 254 is provided to apply measuring beams to the absorbance measuring cell 252. Deuterium and tungsten lamps can alternatively be employed on shorter and longer wavelength sides respectively as measuring light sources. However, the xenon lamp which can cover the range of wavelengths required for measurement is preferably employed since the structure is complicated when such two types of light sources are employed. A xenon flash lamp is preferable since a xenon lamp which is continuously turned on is heated to a high temperature and has a short life. The xenon flash lamp 254 has small heat generation, and a long life. Numeral 256 denotes a power source for the light source.

The absorbance measuring cell 252 is connected with a color developer supply pipe 224 for supplying color developers 218 and 220 through a peristaltic pump 222. The color developers 218 and 220, which react with phosphoric ions, are prepared from an ammonium molybdate solution and an L-ascorbic acid solution respectively. The color developers 218 and 220 may be supplied to the oxidative reaction vessel 204, in place of the absorbance measuring cell 252.

An ultraviolet transmittable quartz window is arranged on a measuring optical path of the absorbance measuring cell 252. The absorbance measuring cell 252 has a path length of 10 mm. A half mirror 262 is set on a transmission optical path of the absorbance measuring cell 252 for separating transmitted light, while a condenser lens 258 of quartz is arranged on the optical path between the absorbance measuring cell 252 and the half mirror 262, so that light transmitted through the absorbance measuring cell 252 is condensed on the half mirror 262. A calibration filter 260 is arranged on an optical path between the condenser lens 258 and the half mirror 262.

The half mirror 260 is prepared from that whose wavelength characteristics are so set that reflected light has a wavelength of at least 800 nm and transmitted light has a wavelength of not more than 240 nm. Transmission and reflection optical paths of the half mirror 262 are adapted to measure a nitrogen compound and a phosphorus compound respectively. A silicon photodiode 266 is arranged on the transmission optical path of the half mirror 262 as a nitrogen side photodetector, while an optical filter 264 having a transmission wavelength of 220 nm is arranged on the optical path between the half mirror 262 and the photodiode 266. On the other hand, a silicon photodiode 270 is arranged on the reflection optical path of the half mirror 262 as a phosphorus side photodetector, and an optical filter 268 having a transmission wavelength of 880 nm is arranged on the optical path between the half mirror 262 and the photodiode 270. The optical filters 264 and 268 have half-band widths of 10 to 30 nm. The silicon photodiodes 266 and 270 serving as photodetectors are prepared from those having wide-range sensitivity over ultraviolet to near infrared regions.

Preamplifiers 272 and 274 are connected to the photodiodes 266 and 270 for amplifying detection outputs thereof respectively, so that the detection outputs amplified by the preamplifiers 272 and 274 are incorporated in an operation part 278 through a pretreatment circuit 276. The pretreatment part 276 makes differential amplification and logarithmic amplification, and the operation part 278 calculates concentration values of the nitrogen compound and the phosphorus compound, to display the same on a display part 280. Numeral 284 denotes a power source for the operation part 278. The measured values can also be taken out as analog outputs, as values of DC 0 to 1 V or DC 4 to 20 mA, for example. Temperature control in measurement and sequence control for the respective electromagnetic valves (pinch and electromagnetic valves), the peristaltic pump and an air pump are carried out by a control part 282.

The operation of the embodiment shown in FIGS. 15 and 16 is now described.

The heater 230 of the photooxidative reaction part 202 is turned on to attain temperature control of 90° C.. At the same time, the power source 228 for the light source is also turned on to stabilize the ON state of the low pressure mercury lamp 226.

As to the sample water, the valves V3 and V4 are previously brought into OFF and ON states respectively for discharging. Thereafter the valves V3 and V4 are brought into ON and OFF states respectively while the valve 250 is brought into an OFF state to introduce the sample water into the reaction vessel 204, and an overflow of the sample water is discharged through the valve V5. Thereafter the valves V3 and V4 are brought into OFF and ON states respectively. Then, the valve V1 is brought into an ON state to introduce air into the reaction vessel 204, and the sample water held by the photooxidative reaction part 202 is irradiated with ultraviolet radiation for about 20 minutes with aeration, to make simultaneous oxidative reaction of a nitrogen compound and a phosphorus compound contained in the sample water.

After completion of photooxidative reaction, the valve V6 is brought into an ON state to introduce half the sample water from the oxidative reaction vessel 204 into the measuring cell 252, and an overflow from the measuring cell 252 is discharged through the valve V7. The sample water held in the measuring cell 252 is irradiated with a measuring beam from the light source 254, to be subjected to measurement of nitric acid ion concentration at a wavelength of 220 nm.

After photoabsorption measurement of the nitric acid ions is completed in the measuring cell 252, the valve V8 is brought into an ON state to discharge the sample water from the measuring cell 252. At this time, the valve V6 is in an OFF state. After the sample water is completely discharged from the measuring cell 252, the valves V8 and V6 are brought into OFF and ON states respectively to introduce the remaining sample water from the photooxidative reaction part 202 into the sample cell 252, and an overflow is discharged through the valve V7. The color developers 218 and 220 are added to the measuring cell 252 for color development. Phosphoric acid ions are measured at a wavelength of 880 nm. After the measurement, the valve V8 is brought into an ON state to discharge the sample water from the measuring cell 252.

Thereafter the valve V2 is brought into an ON state while the valve V6 remains in the OFF state, to supply clean water to the oxidative reaction vessel 204 to wash the same. Then, the valve V6 is brought into an ON state to supply the wash water also to the measuring cell 252 through the oxidative reaction vessel 204, to wash the same. At this time, the valves V8 and V7 are brought into OFF and ON states respectively. After the measuring cell 252 is washed, supply of the wash water is stopped and the valve V8 is brought into an ON state to discharge the wash water from the measuring cell 252. Thus, the wash water is entirely discharged from the measuring system.

Thereafter the process returns to the step of introducing sample water into the photooxidative decomposer 202, to repeat measurement.

Figure 17A:
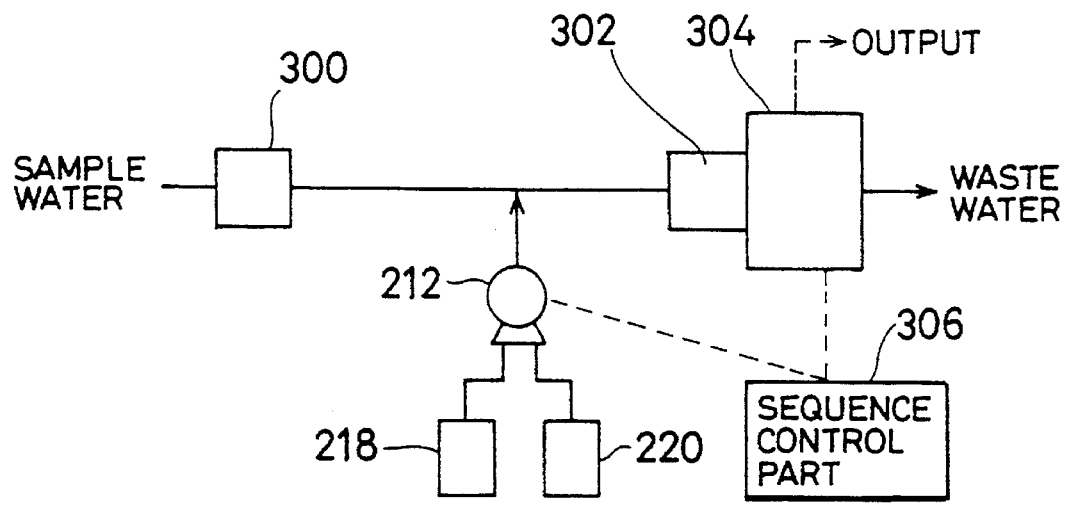
FIG. 17A is a passage diagram schematically showing a flow-type analyzer according to an embodiment of the present invention.
Figure 17B:
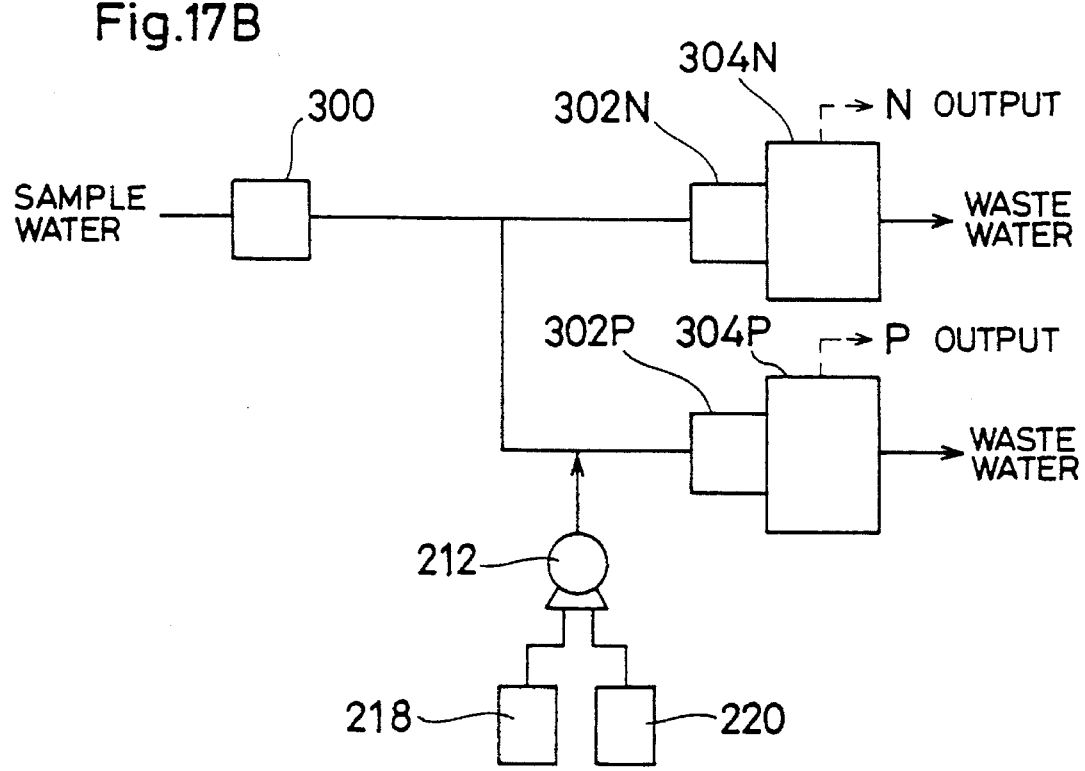
FIG. 17B is a passage diagram schematically showing a flow-type analyzer according to another embodiment of the present invention.

FIGS. 17A and 17B illustrate exemplary analyzers for nitrogen compounds and phosphorus compounds employing flow-type photooxidative decomposers. The flow-type decomposers are different in passage structure from the batch type decomposer.

Referring to FIG. 17A, sample water from a photooxidative decomposer 300 is continuously fed to a measuring cell 302, so that absorbance of nitric ions is measured by an absorbance spectrometer 304 in nitrogen measurement with no operation of a pump 212 and no supply or color developers 218 and 220. In phosphorus measurement, on the other hand, the pump 212 operates to supply the color developers 218 and 220 to a passage between the photooxidative decomposer 300 and the measuring cell 302, so that absorbance of the as-colored solution is measured by the absorbance spectrometer 304. A sequence control part 306 controls the operation of the pump 212 and switching of measuring wavelengths of the absorbance spectrometer 304.

Referring to FIG. 17B, sample water from a photooxidative decomposer 300 is separated into two passages, and one of the passages is directly guided to a measuring cell 302N so that absorbance of nitric acid ions is measured by an absorbance spectrometer 304N. Color developers 218 and 220 are regularly supplied to the other passage from a pump 212, so that absorbance of the sample water which is introduced into a measuring cell 302P is measured by an absorbance spectrometer 304P.

In the structure shown in FIG. 17B, it is possible to simultaneously measure a nitrogen compound and a phosphorus compound in a parallel manner.

Figure 18:
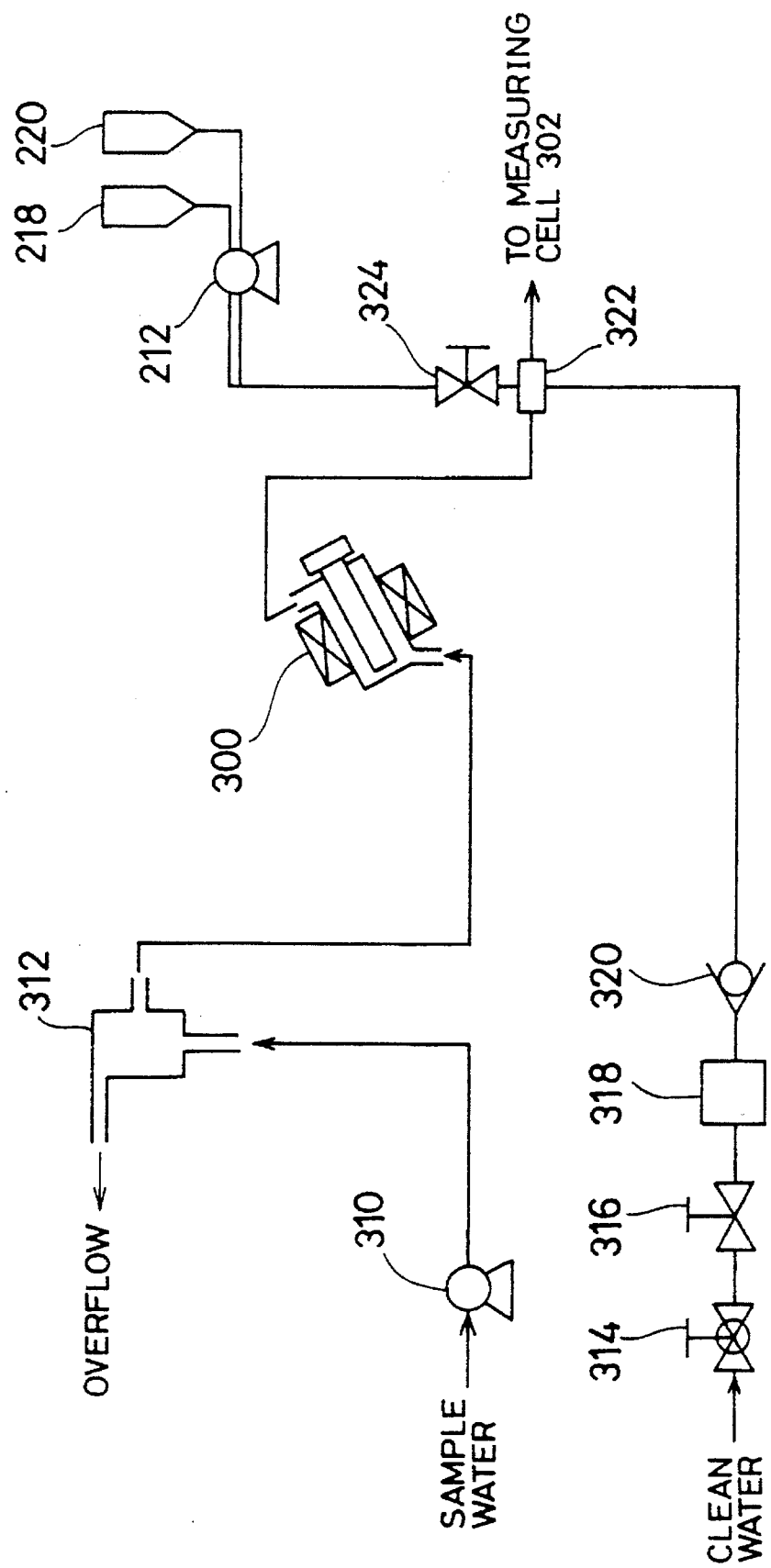
FIG. 18 is a passage diagram showing a reaction part in a flow-type analyzer.

FIG. 18 shows a reaction part of FIG. 17A in detail. The sample water is fed by a pump 310, and adjusted to a prescribed flow rate by an adjusting vessel 312. The sample water is guided from the adjusting vessel 312 to a flow-type photooxidative decomposer 300. The photooxidative decomposer 300 is that illustrated in FIG. 14A to 14D. A sample water passage from the photooxidative decomposer 300 is connected to a manifold 322. In order to supply clean water for washing a measuring cell 302, a clean water supply path meets the sample water passage at the manifold 322 through a ball valve 314, an electromagnetic valve 316, a demineralizer 318 and a check valve 320. Color developers 218 and 220 are supplied through a pump 212, to meet the manifold 322 through a valve 324. A passage from the manifold 322 is guided to the measuring part shown in FIG. 16.

Figure 19:
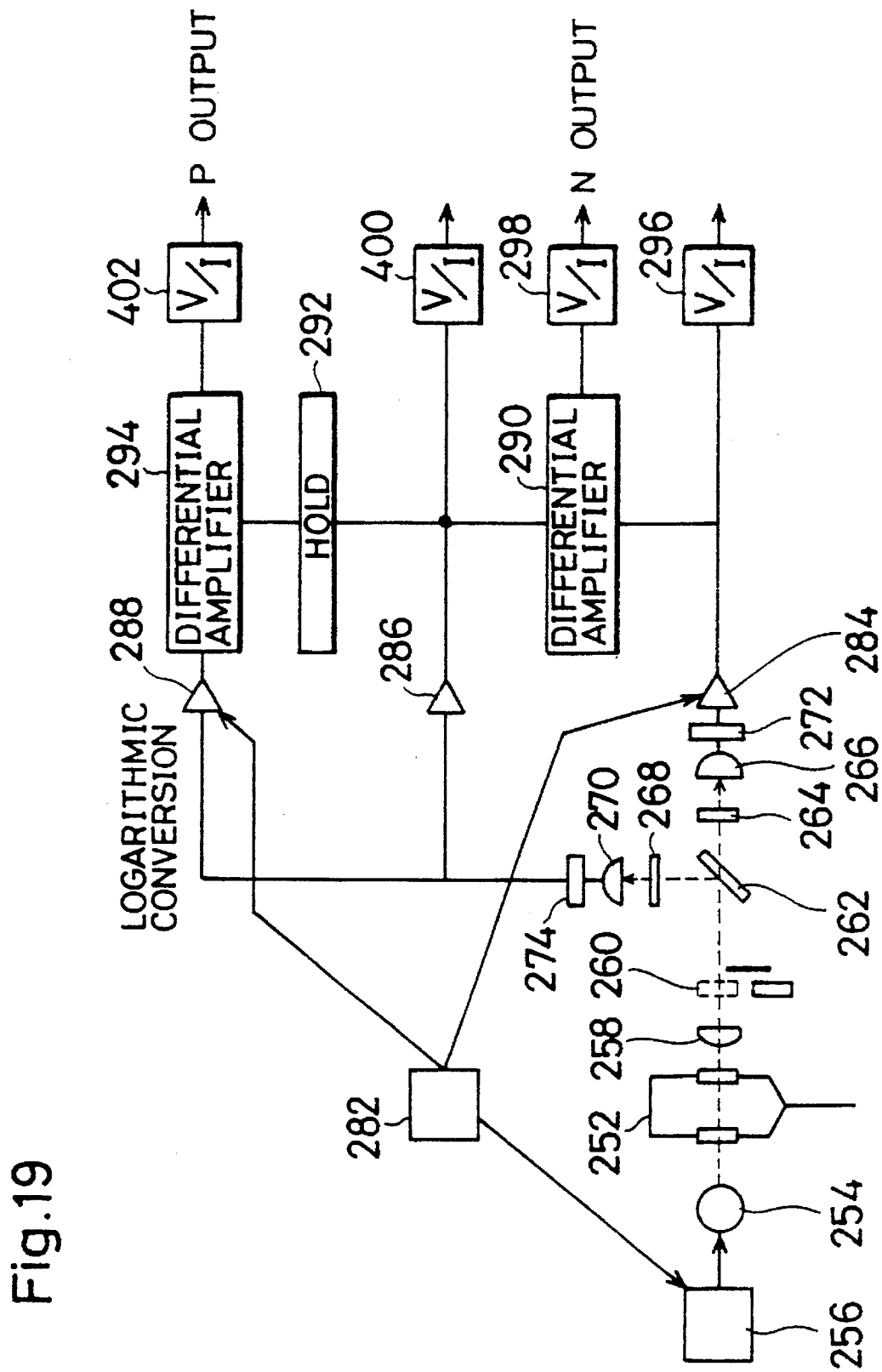
FIG. 19 is a block diagram showing an optical system and a signal processing system in the measuring part shown in FIG. 16.

FIG. 19 illustrates the pretreatment part 276 and the operation part 278 provided in the measuring part shown in FIG. 16 in detail. A detection signal from the nitrogen side photodiode 266 is amplified by the preamplifier 272, and a logarithmic amplifier 284 is connected to the output side of the preamplifier 272 in order to convert the amplified output to a logarithmic value. The output of the logarithmic amplifier 284 is converted to a current value by a V-I converter 296, to be taken out as an output. On the phosphorus side, logarithmic amplifiers 286 and 288 are connected in parallel with the output side of the preamplifier 274, in order to convert a detection output amplified by the preamplifier 274 to a logarithmic value. The output of the logarithmic amplifier 286 is also converted to a current value by a V-I converter 400, so that the output can be taken out. Since the relations between concentration values and absorbance values of a nitrogen compound and a phosphorus compound comply with the Lambert-Beer's law, the signals from the photodiodes 266 and 270 are logarithmically converted so that the output signals are proportionate to the concentration values.

Numeral 290 denotes a nitrogen side differential amplifier, which can amplify the difference between the logarithmic values converted by the logarithmic amplifiers 284 and 286 to take out the output from a V-I converter 298 as a nitrogen side measurement value. The logarithmically converted value from the logarithmic amplifier 286 is also held by a holding circuit 292, while a phosphorus side differential amplifier 294 receives a phosphorus side measurement value from the logarithmic amplifier 288 as well as the output of the logarithmic amplifier 286 in phosphorus side measurement held in the holding circuit 292 to amplify the difference therebetween, for outputting the result from a V-I converter 402 as a phosphorus side measurement value.

In measurement of nitrogen compound concentration, light transmitted through the half mirror 262 serves as sample light while reflected light serves as reference light. The difference between simultaneous detection signals of the photodiodes 266 and 270 is obtained by the differential amplifier 290, and outputted from the V-I converter 298 as a nitrogen compound concentration measurement value.

In measurement of phosphorus compound concentration, a detection signal by the photodiode 270 in measurement of nitrogen compound concentration is held by the holding circuit 292 as reference light, light reflected by the half mirror 262 through a measurement solution (obtained by adding color developers to the sample water) in phosphorus compound measurement serves as sample light, and the difference between the signal from the logarithmic amplifier 288 and that held by the holding circuit 292 is amplified by the differential amplifier 294 and outputted from the V-I converter 402 as a phosphorus compound concentration measurement value.

Samples were irradiated with ultraviolet radiation under presence of photooxidative catalysts with flow of air at about 10 ml/min., to be subjected to measurement of nitrogen compounds and phosphorus compounds according to the present invention.

Table 4 shows the results of standard samples, which were prepared by dissolving reagents in pure water.

TABLE 4

| Standard Sample | Prepared Concentration | Measured Concentration |
|---|---|---|
| Ammonium sulfate $(NH_4)_2SO_4$ | 1.5 ppmN | 1.47 ppmN |
| Sulfanilic acid amide $NH_2C_6H_4SO_2NH_2$ | 1.5 ppmN | 1.58 ppmN |
| L-Sodium glutamate $C_5H_8NO_4Na.H_2O$ | 1.5 ppmN | 1.59 ppmN |
| Adenisine-5-monophosphate $C_{10}H_{14}N_5O_7P$ | 0.8 ppmP | 0.83 ppmP |
| Sodium glycerol phosphate $HOCH_2CH(OH)CH_2OPO_3Na.6H_2O$ | 0.8 ppmP | 0.86 ppmP |
| Sodium phenylphosphate $C_6H_5Na_2PO_4.2H_2O$ | 0.8 ppmP | 0.84 ppmP |

Table 5 shows measurement values of waste water samples prepared by diluting factory effluents with pure water, in comparison of those measured by official and inventive methods.

TABLE 5

| Sample | Official method | | Inventive method | |
|---|---|---|---|---|
| Food factory effluent | 9.19 ppmN | 0.076 ppmP | 9.68 ppmN | 0.080 ppmP |
| Dye factory effluent | 4.64 ppmN | 1.8 ppmP | 6.78 ppmN | 1.63 ppmP |
| Milk factory effluent | 15.7 ppmN | 2.7 ppmP | 17.2 ppmN | 2.89 ppmP |
| Sewage | 27.8 ppmN | 1.0 ppmP | 26.8 ppmN | 1.30 ppmP |
| Machine factory effluent | 13.1 ppmN | 0.40 ppmP | 14.2 ppmN | 0.500 ppmP |

Figure 20A:
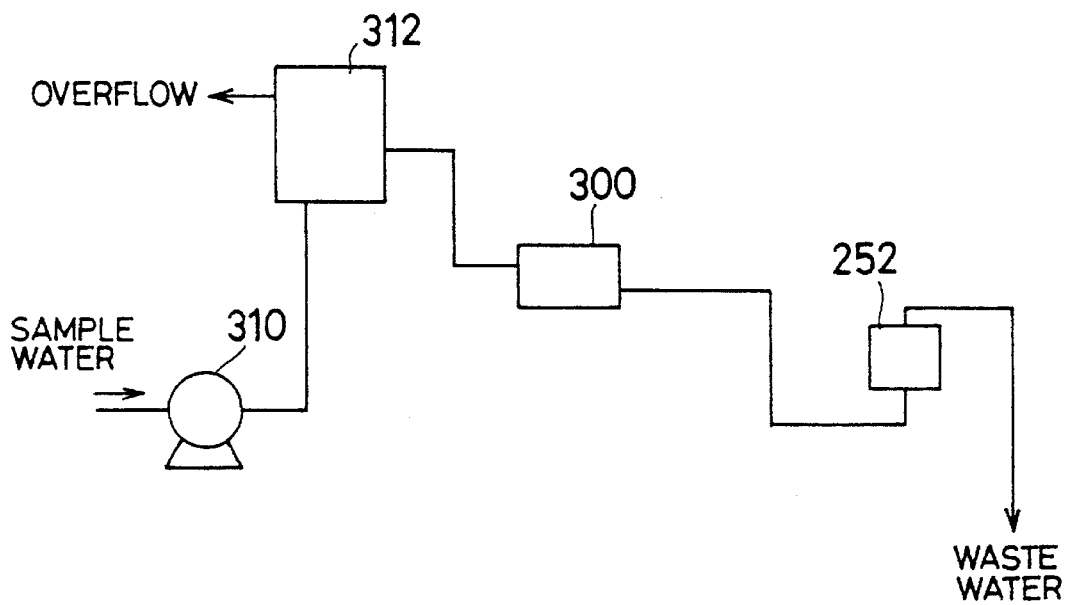
FIG. 20A is a passage diagram showing a first example of flowing sample water through difference in vertical positions in a flow-type analyzer.
Figure 20B:
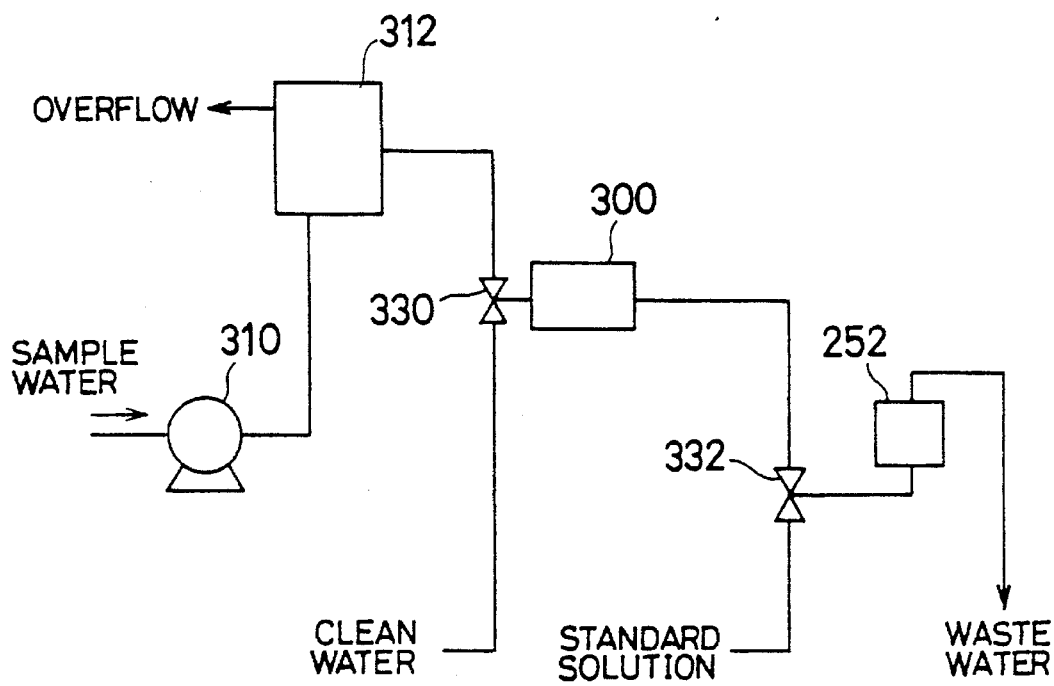
FIG. 20B is a passage diagram showing a second example of flowing sample water through difference in vertical positions in a flow-type analyzer.

FIGS. 20A and 20B show embodiments of inventive analyzers for feeding sample water through vertical differences between passages.

Referring to FIG. 20A, an adjusting vessel 312 is arranged at the highest position and a flow-type photooxidative decomposer 300 to be supplied with sample water from the adjusting vessel 312 is arranged at a lower position, while a measuring cell 252 to be supplied with the sample water photooxidized in the photooxidative decomposer 300 is arranged at a further lower position.

The sample water is fed to the adjusting vessel 312 by a pump 310, and adjusted to be at a prescribed flow rate. The sample water fed from the adjusting vessel 312 is guided to the photooxidative decomposer 300 by the head. The sample water photooxidatively decomposed by the photooxidative decomposer 300 flows to the measuring cell 252 also by the head, to be discharged to a drain from the measuring cell 252.

Referring to FIG. 20B, a clean water supply passage is connected to a passage between an adjusting vessel 312 and a photooxidative decomposer 300 through a switching valve 330, while a standard solution supply passage is connected to a passage between the photooxidative decomposer 300 and a measuring cell 252 through a switching valve 332. The switching valves 330 and 332 are set on sample water passages when measurement is carried out with flow of the sample water, while the switching valve 330 is switched to the clean water supply passage when clean water is supplied for washing the passage and the switching valve 332 is switched to the standard solution supply passage when a standard solution is measured. The sample water flows from the adjusting vessel 312 toward a downstream side by the head also in this case.

Figure 21A:
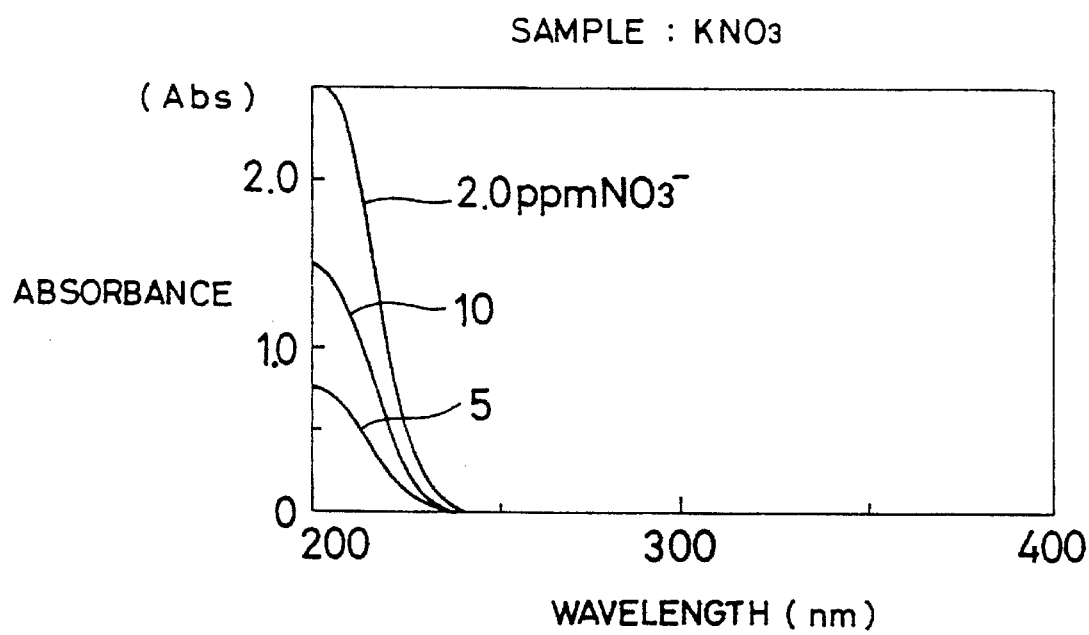
FIG. 21A illustrates absorption spectra of nitric acid ions.
Figure 21B:
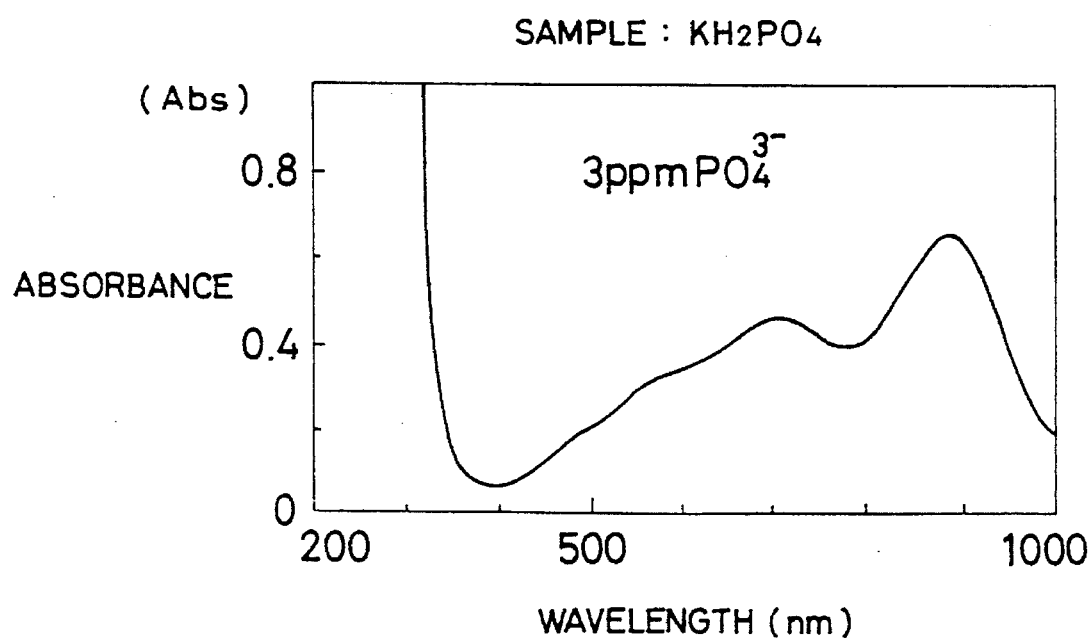
FIG. 21B illustrates absorption spectra of a phosphoric acid ion solution mixed with a color developer.

FIGS. 21A and 21B show absorption spectra in measurement of nitric acid ions and phosphoric acid ions. Referring to FIG. 21A, standard water samples containing $KNO_3$ in concentration values of 5 ppm, 10 ppm and 20 ppm respectively were measured as standard samples of nitric acid ions. Due to absorbance of not more than 240 nm, light of 220 nm in wavelength is selected by the optical filter 264. Referring to FIG. 21B, a standard sample was prepared by adding molybdenum blue (solutions of ammonium molybdate and L-ascorbic acid) as a color developer to sample water containing 3 ppm of $KH_2PO_4$. Light of 880 nm in wavelength is selected by the optical filter 268 for phosphoric acid ion measurement.

While a photooxidative decomposer is employed as a reaction vessel for oxidizing a nitrogen compound and a phosphorus compound in each of the aforementioned embodiments, the reaction vessel may be of another type so far as the same simultaneously oxidizes a nitrogen compound and a phosphorus compound to generate nitric acid ions and phosphoric acid ions respectively.

Figure 22:
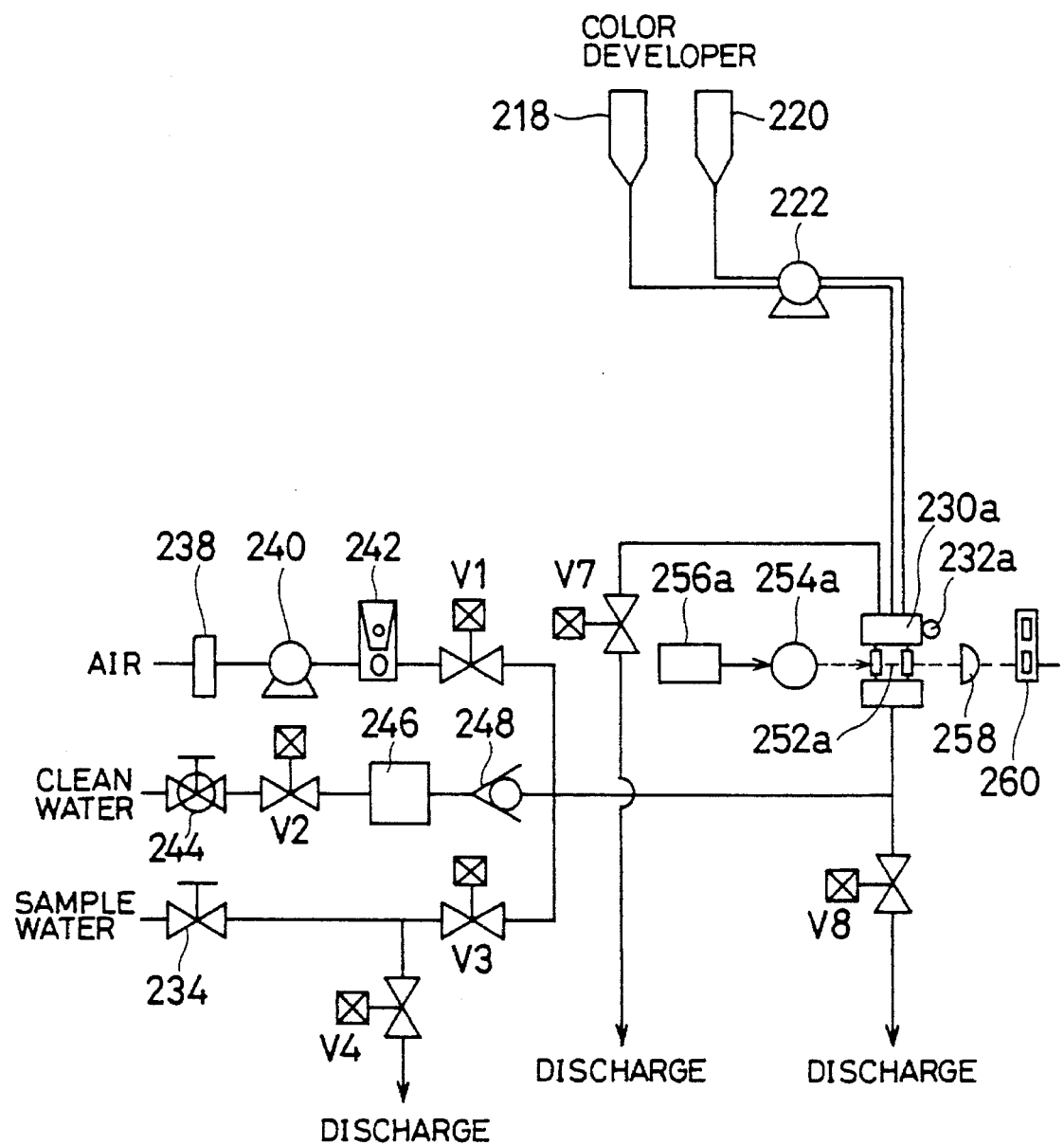
FIG. 22 is a passage diagram showing a reaction part in an embodiment serving both as an oxidative reaction vessel and a measuring cell.

FIG. 22 shows such an embodiment that a measuring cell 252a also serves as a photooxidative decomposer. The measuring cell 252a has a window of ultraviolet transmitting quartz glass, so that light of a xenon lamp 254a serving both as a photooxidative reaction light source and an absorbance measuring light source is incident upon the window. The measuring cell 252a is supplied with sample water and air, as well as clean water for washing. A heater 230a and a temperature detector 232a are provided on the measuring cell 252a, in order to heat the sample water in photooxidative reaction. Color developers 218 and 220 for phosphoric acid ion measurement are supplied to the measuring cell 252a through a peristaltic pump 222.

An optical system for measuring nitrogen compound concentration and phosphorus compound concentration through the measuring cell 252a is identical to that shown in FIG. 16. The light source 254a is formed by a continuous emission xenon lamp, since the same requires a large light quantity for serving both as a photooxidative reaction light source and an absorbance measuring light source.

In the embodiment shown in FIG. 22, the sample water is introduced into the measuring cell 252a and air is blown into the sample water to aerate the same, thereby causing photooxidative reaction over 20 to 30 minutes. Thereafter absorbance measurement at 220 nm is first carried out to measure nitrogen compound concentration. Thereafter constant amounts of the color developers 218 and 220 are injected into the measuring cell 252a and stood still for about 5 minutes, and phosphorus compound concentration is measured by absorbance measurement at 880 nm.

Figure 23:
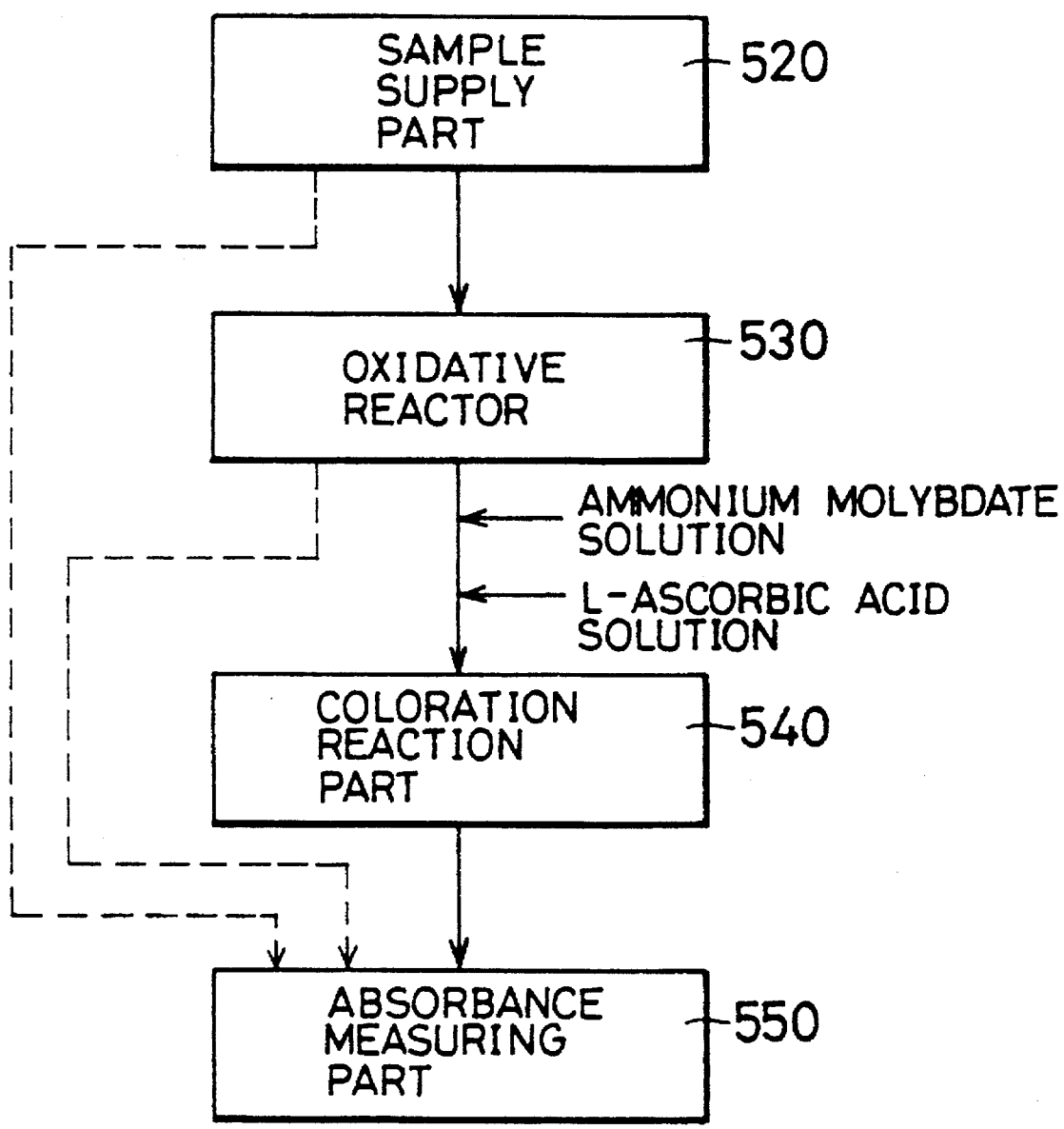
FIG. 23 is a block diagram schematically showing an embodiment which can measure a nitrogen compound and a phosphorus compound as well as an organic pollutant.
Figure 24:
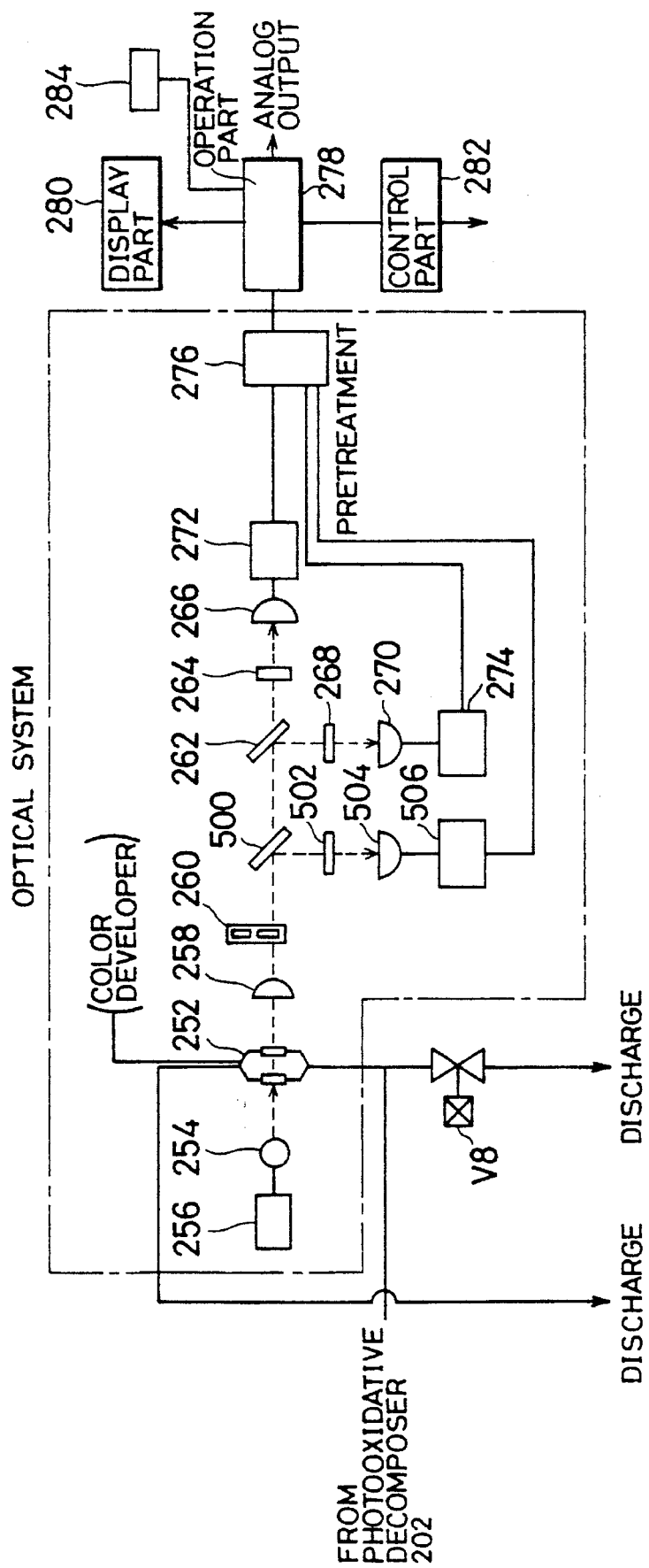
FIG. 24 is a block diagram showing an optical system and a signal processing system in the embodiment shown in FIG. 23.
Figure 25:
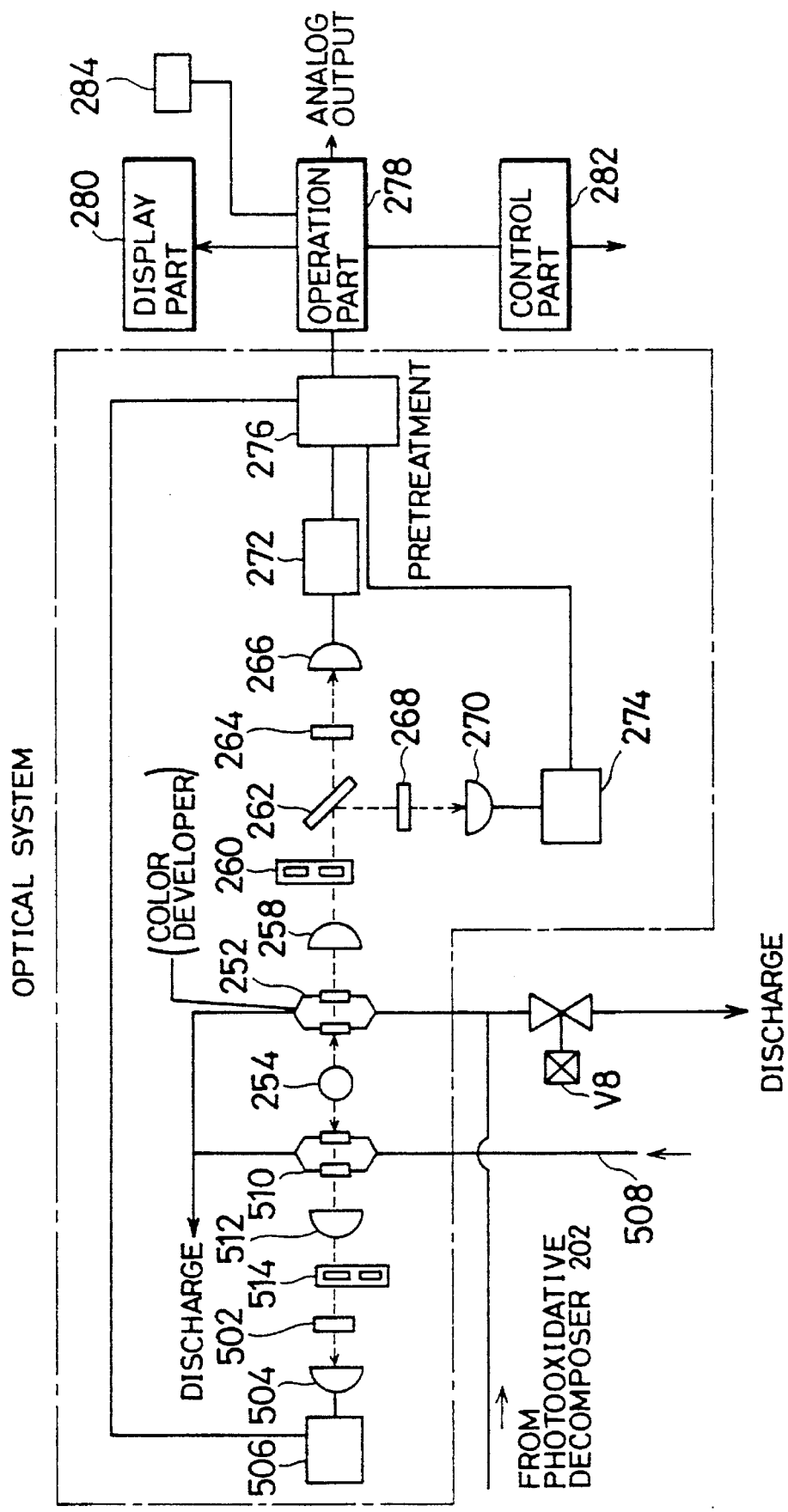
FIG. 25 is a block diagram showing an optical system and a signal processing system in another embodiment.

FIGS. 23 to 25 show embodiments for measuring nitrogen compounds and phosphorus compounds as well as organic pollutants by single measuring apparatuses.

FIG. 23 shows a basic structure of one of the embodiments. This measuring apparatus is mainly formed by a sample supply part 520 for supplying a sample to be measured, an oxidative reactor 530 receiving the sample from the sample supply part 520 and oxidizing the same in measurement of a nitrogen compound or a phosphorus compound, a coloration reaction part 540 for adding an ammonium molybdate solution and an L-ascorbic acid solution to the oxidized sample solution in measurement of a phosphorus compound, and an absorbance measuring part 550 for measuring absorbance of each sample solution.

In order to measure an organic pollutant, a sample is supplied from the sample supply part 520 to the absorbance measuring part 550. At this time, the oxidative reactor 530 and the coloration reaction part 540 merely passes the sample solution or directly supply the sample to the absorbance measuring part 550 through a bypass passage. The absorbance measuring part 550 measures absorbance at a measuring wavelength of 254 nm, for example, to measure the organic pollutant.

In order to measure a nitrogen compound, a sample is fed to the oxidative reactor 530 so that the nitrogen compound is oxidized to nitric acid ions, and the sample solution oxidized in the oxidative reactor 530 is passed through the coloration reaction part 540 or guided to the absorbance measuring part 550 through the bypass passage, so that the nitric acid ions are measured at a measuring wavelength of 220 nm.

In order to measure a phosphorus compound, a sample is fed to the oxidative reactor 530 so that the phosphorus compound is oxidized to phosphoric acid ions and colored by addition of color developers in the coloration reaction part 540, and thereafter the phosphoric acid ions are measured by the absorbance measuring part 550 at a measuring wavelength of 880 nm.

An exemplary reaction part comprising sample supply part 520 and oxidative reactor 530 is that shown in FIG. 15, and a measuring part comprising coloration reaction part 540 and absorbance measuring part 550 is that shown in FIG. 24.

Referring to FIG. 24, the absorbance measuring cell 252 can make sample water flow, and comprises a transmission window of quartz glass for transmitting measuring beams over ultraviolet and near infrared regions. A xenon flash lamp 254 is provided in order to irradiate the absorbance measuring cell 252 with a measuring beam. Deuterium and tungsten lamps may alternatively be employed on shorter and longer wavelength sides respectively as measuring light sources. Numeral 256 denotes a power source for the light source.

While means for adding color developers is provided on the absorbance measuring cell 252, the same may alternatively provided on an oxidative reaction vessel 204.

The absorbance measuring cell 252 has the ultraviolet transmittable quartz window which is arranged on a measuring optical path, and its optical path length is 10 mm. A half mirror 500 is arranged on a transmission optical path of the absorbance measuring cell 252 for separating transmitted light, and a condenser lens 258 of quartz is arranged on an optical path between the absorbance measuring cell 252 and the half mirror 500, so that light transmitted through the absorbance measuring cell 252 is condensed on the half mirror 262. A calibration filter 260 is arranged on an optical path between the condenser lens 258 and the half mirror 500.

The half mirror 500 has no wavelength characteristics, but is merely adapted to separate light transmitted through the absorbance measuring cell 252 into reflected light and transmitted light. A silicon photodiode 504 is arranged on a reflection optical path of the half mirror 500 in order to measure the organic pollutant, while an optical filter 502 having a transmission wavelength of about 254 nm is arranged on an optical path between the half mirror 500 and the photodiode 504.

The half mirror 262 is further arranged on a transmission optical path of the half mirror 500. An optical system of reflection and transmission optical paths of the half mirror 262 and a signal processing system are similar to those shown in FIG. 16.

The operation of the embodiment of FIG. 15 and FIG. 24 is now described.

First, valves V3 and V4 are brought into OFF and ON states to discharge sample water. In order to measure an organic pollutant, valves V3, V4, 250, V5 and V6 are brought into ON, OFF, OFF, OFF and ON states respectively for introducing sample water into the measuring cell 252 through the oxidative reaction vessel 204 while discharging an overflow from the measuring cell 252. The sample held in or flowing in the sample cell 252 is irradiated with a measuring beam from the light source 254, so that the organic pollutant is measured at a wavelength of 254 nm.

A nitrogen compound and a phosphorus compound are measured by an operation which is identical to that of the embodiment shown in FIGS. 15 and 16.

A photooxidative decomposer 202 may be formed by providing $TiO_2$ or silver halide in the oxidative reaction vessel 204 as a photooxidation catalyst, to increase the reaction rate.

In the embodiment shown in FIG. 15 and FIG. 24, the sample water is guided to the measuring cell 252 through the reaction vessel 204 also in measurement of the organic pollutant. In an embodiment comprising a measuring part shown in FIG. 25, on the other hand, measuring cells 252 and 510 are provided independently of each other for measuring a nitrogen compound and a phosphorus compound, and an organic pollutant respectively. While a reaction part is formed by that shown in FIG. 15, the sample water supply passage 508 shown by chain lines in FIG. 15 is branched from a portion between the valves 234 and V3 so that sample water is directly guided to the measuring cell 510 without passing through the reaction vessel 204.

A light source 254 for measurement is utilized by the measuring cells 252 and 510 in common, while optical systems 268 and 270 for nitrogen compound measurement and optical systems 264 and 266 for phosphorus compound measurement are arranged on a transmission optical path of the measuring cell 252, and an optical filter 502 and a silicon photodiode 504 are arranged on a transmission optical path of the measuring cell 510 for carrying out measurement at an absorption wavelength of an organic pollutant through a condenser lens 512 and a calibration filter 514.

In the embodiment shown in FIG. 25, the measuring cells 252 and 510 are provided independently of each other, whereby it is possible to measure the organic pollutant in continuation. A nitrogen compound and a phosphorus compound are intermittently measured.

The inventive analytical method may not be necessarily employed under conditions for attaining recovery of 100%. The method can also be employed in a state of recovery of less than 100%, by previously measuring a constant correlation between analytical values measured by a conventionally established method employing oxidation with an oxidant and absorptiometry and in the inventive method in a state with recovery of less than 100%.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An analytical method of analyzing a nitrogen compound and a phosphorus compound being contained in water, comprising the following steps (A) to (C):

(A) an oxidation step of irradiating sample water with ultraviolet radiation while heating said sample water to 50° to 100° C.;

(B) a step of measuring nitric acid ions being contained in oxidized said sample water by absorptiometry; and (C) a step of adding molybdenum blue selectively reacting with phosphoric acid ions to oxidized said sample water and measuring the as-colored solution by absorptiometry.

2. An analytical method in accordance with claim 1, wherein said oxidation step of irradiating said sample water with ultraviolet radiation is carried out while blowing a gas containing oxygen or ozone into said sample water.

3. An analytical method in accordance with claim 1, wherein said oxidation step of irradiating said sample water with ultraviolet radiation is carried out under presence of a photooxidation catalyst.

4. An analytical method in accordance with claim 3, wherein said photooxidation catalyst is $TiO_2$ or silver halide.

5. An analytical method in accordance with claim 1, further comprising a first step of:

providing a photooxidative decomposer, said photooxidative decomposer comprising an oxidative reaction vessel having a sample water inlet/outlet;

heating means for heating sample water being stored in said oxidative reaction vessel to 50° to 100° C.; and an ultraviolet radiation source for irradiating said sample water being stored in said oxidative reaction vessel and heated by said heating means with ultraviolet radiation for oxidizing both of a nitrogen compound and a phosphorus compound being contained in said sample water into nitric acid ions and phosphoric acid ions respectively, wherein said oxidation step is performed by using said photooxidative decomposer.

6. An analytical method in accordance with claim 5, wherein said oxidative reaction vessel comprises a gas supply port for blowing gas containing oxygen or ozone into said sample water.

7. An analytical method in accordance with claim 5, wherein said oxidative reaction vessel is provided with a photooxidation catalyst thin film on its inner surface, or charged with a photooxidation catalyst in its interior.

8. An analytical method in accordance with claim 7, wherein said photooxidation catalyst is silver halide.

9. An analytical method in accordance with claim 7, wherein said photooxidation catalyst is titanium dioxide.

10. An analytical method in accordance with claim 9, wherein said titanium dioxide is anatase titanium dioxide.

11. An analytical method in accordance with claim 7, wherein said photooxidation catalyst is prepared by adding platinum to anatase titanium oxide.

12. An analytical method in accordance with claim 7, wherein said photooxidation catalyst is prepared by adding platinum and ruthenium dioxide to anatase titanium dioxide.

13. An analytical method in accordance with claim 7, wherein said photooxidation catalyst thin film is formed on an inner surface of said oxidative reaction vessel, said photooxidation catalyst thin film consisting of a coating film being prepared by firing a sol of silicon alkoxide containing anatase titanium dioxide powder, ruthenium dioxide powder and chloroplatinic acid being added thereto.

14. An analytical method in accordance with claim 5, wherein said oxidative reaction vessel is provided with a photooxidation catalyst thin film on its inner surface or charged with a photooxidation catalyst in its interior, said oxidative reaction vessel comprising a passage to and from which said sample water is discontinuously supplied and discontinuously taken out.

15. An analytical method in accordance with claim 5, wherein said oxidative reaction vessel is provided with a photooxidation catalyst thin film on its inner surface or charged with a photooxidation catalyst in its interior, said oxidative reaction vessel comprising a passage to and from which said sample water is continuously supplied and continuously taken out.

* * * * *

UNITED STATES PATENT AND TRADEMARK OFFICE
CERTIFICATE OF CORRECTION

PATENT NO. : 5,567,621

DATED : Tahara et al.

INVENTOR(S) : October 22, 1996

It is certified that error appears in the above-indentified patent and that said Letters Patent is hereby corrected as shown below:

Title page, Item [75], line [1], please delete "Yauzo Morita" insert therefor -- Youzo Morita --.

Signed and Sealed this

Twenty-fourth Day of December, 1996

Attest:

BRUCE LEHMAN

*Attesting Officer*   *Commissioner of Patents and Trademarks*